United States Patent
Aoyama

(10) Patent No.: US 11,363,943 B2
(45) Date of Patent: Jun. 21, 2022

(54) ENDOSCOPE SYSTEM AND OPERATING METHOD THEREOF

(71) Applicant: FUJIFILM Corporation, Tokyo (JP)

(72) Inventor: Tatsuya Aoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 532 days.

(21) Appl. No.: 16/388,894

(22) Filed: Apr. 19, 2019

(65) Prior Publication Data

US 2019/0239737 A1 Aug. 8, 2019

Related U.S. Application Data

(63) Continuation of application No. PCT/JP2017/036239, filed on Oct. 5, 2017.

(30) Foreign Application Priority Data

Oct. 27, 2016 (JP) .............................. JP2016-211059

(51) Int. Cl.
*A61B 1/00* (2006.01)
*A61B 1/06* (2006.01)
(Continued)

(52) U.S. Cl.
CPC .............. *A61B 1/0638* (2013.01); *A61B 1/00* (2013.01); *A61B 1/00096* (2013.01);
(Continued)

(58) Field of Classification Search
CPC ......... A61B 1/0638; A61B 1/045; A61B 1/00; A61B 1/00096; A61B 1/00188;
(Continued)

(56) References Cited

U.S. PATENT DOCUMENTS

2004/0059215 A1 3/2004 Nishimura et al.
2011/0034770 A1 2/2011 Endo et al.
(Continued)

FOREIGN PATENT DOCUMENTS

JP 2003126045 5/2003
JP 2011036361 2/2011
(Continued)

OTHER PUBLICATIONS

"International Search Report (Form PCT/ISA/210) of PCT/JP2017/036239," dated Dec. 19, 2017, with English translation thereof, pp. 1-5.
(Continued)

*Primary Examiner* — Timothy J Neal
*Assistant Examiner* — Sung Ham
(74) *Attorney, Agent, or Firm* — JCIPRNET

(57) ABSTRACT

An endoscope system includes a storage medium that stores a plurality of correspondence between an imaging condition and a plurality of index values relating to a plurality of structures of an observation object, wherein the plurality of index values including a first index value acquirable under the first imaging condition and a second index value non-acquirable under the first imaging condition but acquirable under a second imaging condition, a monitor and a processor, coupled to the storage medium and the monitor. The processor is configured to: acquire an image of the observation object by using an endoscope; acquire a first imaging condition which represents an imaging condition of the image; refer to the plurality of index values and the imaging condition in the storage medium and extract the second imaging condition; and display guidance indicating that the second index value is acquirable under the extracted second imaging condition.

22 Claims, 17 Drawing Sheets

(51) Int. Cl.
*A61B 1/045* (2006.01)
*A61B 1/04* (2006.01)

(52) U.S. Cl.
CPC .......... *A61B 1/00188* (2013.01); *A61B 1/045* (2013.01); *A61B 1/0669* (2013.01); *A61B 1/0684* (2013.01); *A61B 1/00009* (2013.01); *A61B 1/043* (2013.01); *A61B 1/0646* (2013.01); *A61B 1/0653* (2013.01)

(58) Field of Classification Search
CPC ..... A61B 1/0669; A61B 1/0684; A61B 1/043; A61B 1/0646; A61B 1/00009; A61B 1/0653; A61B 1/00055; A61B 1/00006; A61B 1/00039; G06T 2207/30028; G06T 2207/30168; G06T 2207/10068; G06T 2207/10152; G06T 2207/30101; G06T 7/0012; H04N 2005/2255
USPC .......................................... 600/300, 301, 322
See application file for complete search history.

(56) References Cited

U.S. PATENT DOCUMENTS

| | | | | |
|---|---|---|---|---|
| 2011/0237884 | A1* | 9/2011 | Saito | A61B 1/063 600/109 |
| 2011/0270035 | A1 | 11/2011 | Gono | |
| 2012/0190922 | A1* | 7/2012 | Kaku | A61B 1/0005 600/109 |
| 2012/0197076 | A1* | 8/2012 | Minetoma | A61B 5/489 600/109 |
| 2012/0302847 | A1 | 11/2012 | Ozawa et al. | |
| 2013/0018242 | A1 | 1/2013 | Yamaguchi et al. | |
| 2013/0245410 | A1* | 9/2013 | Saito | A61B 1/0051 600/339 |
| 2013/0245411 | A1* | 9/2013 | Saito | A61B 1/045 600/339 |
| 2015/0272429 | A1* | 10/2015 | Shigeta | A61B 1/0002 348/65 |
| 2016/0058274 | A1* | 3/2016 | Chiba | A61B 5/14546 600/328 |
| 2017/0014022 | A1* | 1/2017 | Tamura | A61B 1/063 |
| 2018/0289246 | A1* | 10/2018 | Tabata | A61B 1/043 |
| 2018/0368670 | A1* | 12/2018 | Watanabe | A61B 1/0638 |

FOREIGN PATENT DOCUMENTS

| | | |
|---|---|---|
| JP | 2012152332 | 8/2012 |
| JP | 2012239816 | 12/2012 |
| JP | 2013013589 | 1/2013 |
| JP | 2013017769 | 1/2013 |
| JP | 2014212925 | 11/2014 |
| JP | 2015061618 | 4/2015 |
| JP | 2016087370 | 5/2016 |
| WO | 2010116902 | 10/2010 |

OTHER PUBLICATIONS

"Written Opinion of the International Searching Authority (Form PCT/ISA/237) of PCT/JP2017/036239," dated Dec. 19, 2017, with English translation thereof, pp. 1-8.

"Search Report of Europe Counterpart Application", dated Nov. 4, 2019, p. 1-p. 4.

* cited by examiner

FIG. 6

| | IMAGING CONDITION | ACQUIRABLE INDEX VALUE | NON-ACQUIRABLE INDEX VALUE |
|---|---|---|---|
| C11 | LIGHT QUANTITY RATIO; R11<br>OBSERVATION DISTANCE; ENLARGED OBSERVATION DISTANCE<br>ZOOM MAGNIFICATION; LOW MAGNIFICATION | DENSITY OF MIDDLE LAYER BLOOD VESSEL<br>COMPLEXITY OF MIDDLE LAYER BLOOD VESSEL<br>UNIFORMITY OF THICKNESS OF MIDDLE LAYER BLOOD VESSEL | DENSITY OF SURFACE LAYER BLOOD VESSEL<br>COMPLEXITY OF SURFACE LAYER BLOOD VESSEL<br>UNIFORMITY OF SURFACE STRUCTURE |
| C12 | LIGHT QUANTITY RATIO; R12<br>OBSERVATION DISTANCE; ENLARGED OBSERVATION DISTANCE<br>ZOOM MAGNIFICATION; LOW MAGNIFICATION | DENSITY OF SURFACE LAYER BLOOD VESSEL<br>COMPLEXITY OF SURFACE LAYER BLOOD VESSEL<br>UNIFORMITY OF SURFACE STRUCTURE | DENSITY OF MIDDLE LAYER BLOOD VESSEL<br>COMPLEXITY OF MIDDLE LAYER BLOOD VESSEL<br>UNIFORMITY OF THICKNESS OF MIDDLE LAYER BLOOD VESSEL |
| ... | ... | ... | ... |

136 DIAGNOSIS-PURPOSE AND INDEX-VALUE STORAGE UNIT

136a

| FIRST DIAGNOSIS PURPOSE | INDEX VALUE |
|---|---|
| LARGE INTESTINE SCREENING | COMPLEXITY OF SURFACE LAYER BLOOD VESSEL |
| | COMPLEXITY OF MIDDLE LAYER BLOOD VESSEL |
| STOMACH SCREENING | COMPLEXITY OF MIDDLE LAYER BLOOD VESSEL |
| | UNIFORMITY OF SURFACE STRUCTURE |
| LARGE INTESTINE CLOSE INSPECTION | DENSITY OF SURFACE LAYER BLOOD VESSEL |

136b

| SECOND DIAGNOSIS PURPOSE | INDEX VALUE |
|---|---|
| BARRETT'S ESOPHAGUS | DENSITY OF SURFACE LAYER BLOOD VESSEL |
| | COMPLEXITY OF SURFACE LAYER BLOOD VESSEL |
| | DENSITY OF MIDDLE LAYER BLOOD VESSEL |
| | COMPLEXITY OF MIDDLE LAYER BLOOD VESSEL |
| LARGE INTESTINAL POLYPOSIS | UNIFORMITY OF THICKNESS OF MIDDLE LAYER BLOOD VESSEL |
| | UNIFORMITY OF SURFACE STRUCTURE |
| ANGIODYSPLASIA | DENSITY OF MIDDLE LAYER BLOOD VESSEL |

136c

| THIRD DIAGNOSIS PURPOSE | INDEX VALUE |
|---|---|
| REMISSION PERIOD OF ULCERATIVE COLITIS | COMPLEXITY OF SURFACE LAYER BLOOD VESSEL |
| | COMPLEXITY OF MIDDLE LAYER BLOOD VESSEL |
| ACTIVE PERIOD OF ULCERATIVE COLITIS | COMPLEXITY OF SURFACE LAYER BLOOD VESSEL |

FIG. 17

142 DIAGNOSIS-PURPOSE AND INDEX-VALUE STORAGE UNIT

142a

| FIRST DIAGNOSIS PURPOSE | INDEX VALUE | COEFFICIENT |
|---|---|---|
| LARGE INTESTINE SCREENING | COMPLEXITY OF SURFACE LAYER BLOOD VESSEL | 0.5 |
|  | COMPLEXITY OF MIDDLE LAYER BLOOD VESSEL | 1 |
| STOMACH SCREENING | COMPLEXITY OF MIDDLE LAYER BLOOD VESSEL | 1 |
|  | UNIFORMITY OF SURFACE STRUCTURE | 1 |
| LARGE INTESTINE CLOSE INSPECTION | DENSITY OF SURFACE LAYER BLOOD VESSEL | 1 |

142b

| SECOND DIAGNOSIS PURPOSE | INDEX VALUE | COEFFICIENT |
|---|---|---|
| BARRETT'S ESOPHAGUS | DENSITY OF SURFACE LAYER BLOOD VESSEL | 1 |
|  | COMPLEXITY OF SURFACE LAYER BLOOD VESSEL | 1 |
|  | DENSITY OF MIDDLE LAYER BLOOD VESSEL | 1 |
|  | COMPLEXITY OF MIDDLE LAYER BLOOD VESSEL | 1 |
| LARGE INTESTINAL POLYPOSIS | UNIFORMITY OF THICKNESS OF MIDDLE LAYER BLOOD VESSEL | 1 |
|  | UNIFORMITY OF SURFACE STRUCTURE | 0.5 |
| ANGIODYSPLASIA | DENSITY OF MIDDLE LAYER BLOOD VESSEL | 1 |

142c

| THIRD DIAGNOSIS PURPOSE | INDEX VALUE | COEFFICIENT |
|---|---|---|
| REMISSION PERIOD OF ULCERATIVE COLITIS | COMPLEXITY OF SURFACE LAYER BLOOD VESSEL | 1 |
|  | COMPLEXITY OF MIDDLE LAYER BLOOD VESSEL | 1 |
| ACTIVE PERIOD OF ULCERATIVE COLITIS | COMPLEXITY OF SURFACE LAYER BLOOD VESSEL | 1 |

ENDOSCOPE SYSTEM AND OPERATING METHOD THEREOF

CROSS REFERENCE TO RELATED APPLICATIONS

This application is a Continuation of PCT International Application No. PCT/JP2017/036239 filed on Oct. 5, 2017, which claims priority under 35 U.S.C § 119(a) to Patent Application No. 2016-211059 filed in Japan on Oct. 27, 2016, all of which are hereby expressly incorporated by reference into the present application.

BACKGROUND OF THE INVENTION

1. Field of the Invention

The present invention relates to an endoscope system and an operating method of the endoscope system.

2. Description of the Related Art

In medical fields, diagnoses using an endoscope system including a light source device, an endoscope, and a processor device are being widely performed. With an endoscope system, an observation object is irradiated with illumination light emitted by a light source device via an endoscope, an image signal is obtained by image-capturing the observation object illuminated with the illumination light, and a processor device generates an image of the observation object on the basis of the image signal. By displaying the image on a monitor, a doctor can make a diagnosis while watching the image on the monitor.

Also in endoscopic diagnoses in recent years, imaging conditions, such as light source balance of a light source, are being changed in accordance with other various conditions such as a diagnosis purpose (WO2010/116902A, JP2011-036361A, JP2013-017769A, and JP2015-061618A) and guidance suitable for various conditions is being displayed (JP2012-152332A). For example, as described in WO2010/116902A and JP2011-036361A, the balance of light source wavelengths is being changed in accordance with an observation portion or observation magnification for visualization. With WO2010/116902A and JP2011-036361A, to observe a surface layer blood vessel in enlarged observation and to perform overall observation with a hue of white light in non-enlarged observation, illumination is provided by using light with short wavelengths in enlarged observation and illumination is provided by using white light in non-enlarged observation.

In addition, in JP2013-017769A, to increase the calculation accuracy of absorption component density such as oxygen saturation, the wavelength set of a light source is switched on the basis of the difference in absorption component density between a blood vessel region and the other region by preparatory imaging. In addition, in JP2015-061618A, the light source balance of an imaging light source is adjusted in accordance with an observation portion or a model name of an endoscope. In addition, in JP2012-152332A, guidance of the mode of light source balance suitable for observation conditions is displayed on a monitor.

Furthermore, in endoscopic diagnoses in recent years, as described in JP2016-087370A, a diagnosis assisting system is being introduced to fill a difference in skill among doctors. The diagnosis assisting system extracts a feature of a lesion portion from an image obtained by imaging an observation object, indexes the feature, and displays the index.

SUMMARY OF THE INVENTION

Endoscopic diagnoses handle various subject diseases, diagnosis purposes, and stages of diseases to be inspected. The subject diseases and so forth have distinctive structures and features that can be observed depending on imaging conditions, such as a light source and an observation distance. Therefore, to make a diagnosis on a disease by using an endoscope, it is required to set imaging conditions suitable for the structure and feature to be observed. Moreover, a diagnosis may be made using an index value obtained by indexing a structure or a feature using a numerical value. It is also required to set imaging conditions so as to acquire an index value required for making a diagnosis on a disease. Furthermore, if an index value non-acquirable under the current imaging conditions from among index values required for making a diagnosis on a disease, it is requested to acquire even such a non-acquirable index value.

An object of the present invention is to provide an endoscope system and an operating method of the endoscope system that can provide guidance for acquiring an index value non-acquirable under the current imaging conditions.

An endoscope system according to the present invention includes an imaging condition acquisition unit that acquires a first imaging condition as an imaging condition for imaging an observation object by using an endoscope; an index-value and imaging-condition storage unit that stores correspondence between the imaging condition, and, as an index value relating to a structure of the observation object, a plurality of index values including a first index value acquirable under the first imaging condition and a second index value non-acquirable under the first imaging condition but acquirable under a second imaging condition; an imaging condition extraction unit that refers to the index-value and imaging-condition storage unit and extracts the second imaging condition; and a guidance display unit that displays guidance indicating that the second index value is acquirable under the extracted second imaging condition.

Preferably, the endoscope system further includes a diagnosis purpose acquisition unit that acquires a diagnosis purpose; and the imaging condition extraction unit uses the second index value that is non-acquirable under the first imaging condition and that is used for the acquired diagnosis purpose, and extracts the second imaging condition.

Preferably, the diagnosis purpose includes a first diagnosis purpose including screening and close inspection, a second diagnosis purpose relating to a type of disease, and a third diagnosis purpose relating to a stage of disease; and the imaging condition extraction unit extracts the second imaging condition in accordance with at least one diagnosis purpose of the first diagnosis purpose, the second diagnosis purpose, or the third diagnosis purpose.

Preferably, the endoscope system further includes an index value selection unit that uses the acquired first imaging condition, refers to the index-value and imaging-condition storage unit, and selects the first index value; and the guidance display unit further displays guidance indicating that the first index value is acquirable under the acquired first imaging condition.

Preferably, the endoscope system further includes a diagnosis purpose acquisition unit that acquires a diagnosis purpose; and the index value selection unit selects, as the first index value, an index value that is acquirable under the first imaging condition and that is used for the acquired diagnosis purpose.

Preferably, the endoscope system further includes an image acquisition unit that acquires an endoscope image obtained through the imaging; an index value calculation unit that calculates the selected first index value from the endoscope image; and a first emphasis image generation unit that uses the endoscope image and the calculated index value, and generates a first structure emphasis image in which the structure is emphasized.

Preferably, the endoscope system further includes a structure parameter calculation unit that calculates a structure parameter of the structure by weighting the calculated first index value and arithmetically operating the first index value.

Preferably, the endoscope system further includes a second emphasis image generation unit that uses the endoscope image and the calculated structure parameter, and generates a second structure emphasis image in which the structure is emphasized.

Preferably, the guidance display unit displays the acquired first imaging condition.

An operating method of an endoscope system according to the present invention includes a step in which an imaging condition acquisition unit acquires a first imaging condition as an imaging condition for imaging an observation object by using an endoscope; a step in which an imaging condition extraction unit refers to an index-value and imaging-condition storage unit that stores correspondence between the imaging condition, and, as an index value relating to a structure of the observation object, a plurality of index values including a first index value acquirable under the first imaging condition and a second index value non-acquirable under the first imaging condition but acquirable under a second imaging condition, and extracts the second imaging condition; and a step in which a guidance display unit displays guidance indicating that the second index value is acquirable under the extracted second imaging condition.

An endoscope system according to the present invention includes an image acquisition unit that acquires an endoscope image obtained by an endoscope imaging an observation object; an imaging condition acquisition unit that acquires a first imaging condition as an imaging condition for the imaging; an index-value and imaging-condition storage unit that stores correspondence between the imaging condition, and, as an index value relating to a structure of the observation object, a plurality of index values including a first index value acquirable under the first imaging condition and a second index value non-acquirable under the first imaging condition but acquirable under a second imaging condition; an index value selection unit that uses the acquired first imaging condition, refers to the index-value and imaging-condition storage unit, and selects the first index value; an index value calculation unit that calculates the selected first index value from the endoscope image; a first emphasis image generation unit that uses the endoscope image and the calculated index value, and generates a first structure emphasis image in which the structure is emphasized; an imaging condition extraction unit that refers to the index-value and imaging-condition storage unit and extracts the second imaging condition; and a guidance display unit that displays the first structure emphasis image and displays guidance indicating that the second index value is acquirable under the extracted second imaging condition.

With the endoscope system and the operating method of the endoscope system according to the present invention, an index value non-acquirable under current imaging conditions can be acquired.

BRIEF DESCRIPTION OF THE DRAWINGS

FIG. 6 is an illustration explaining an index-value and imaging-condition storage unit;

FIG. 13 is an illustration explaining a diagnosis-purpose and index-value storage unit;

FIG. 17 is an illustration explaining a diagnosis-purpose and index-value storage unit according to a fourth embodiment;

DESCRIPTION OF THE PREFERRED EMBODIMENTS

First Embodiment

Figure 1:
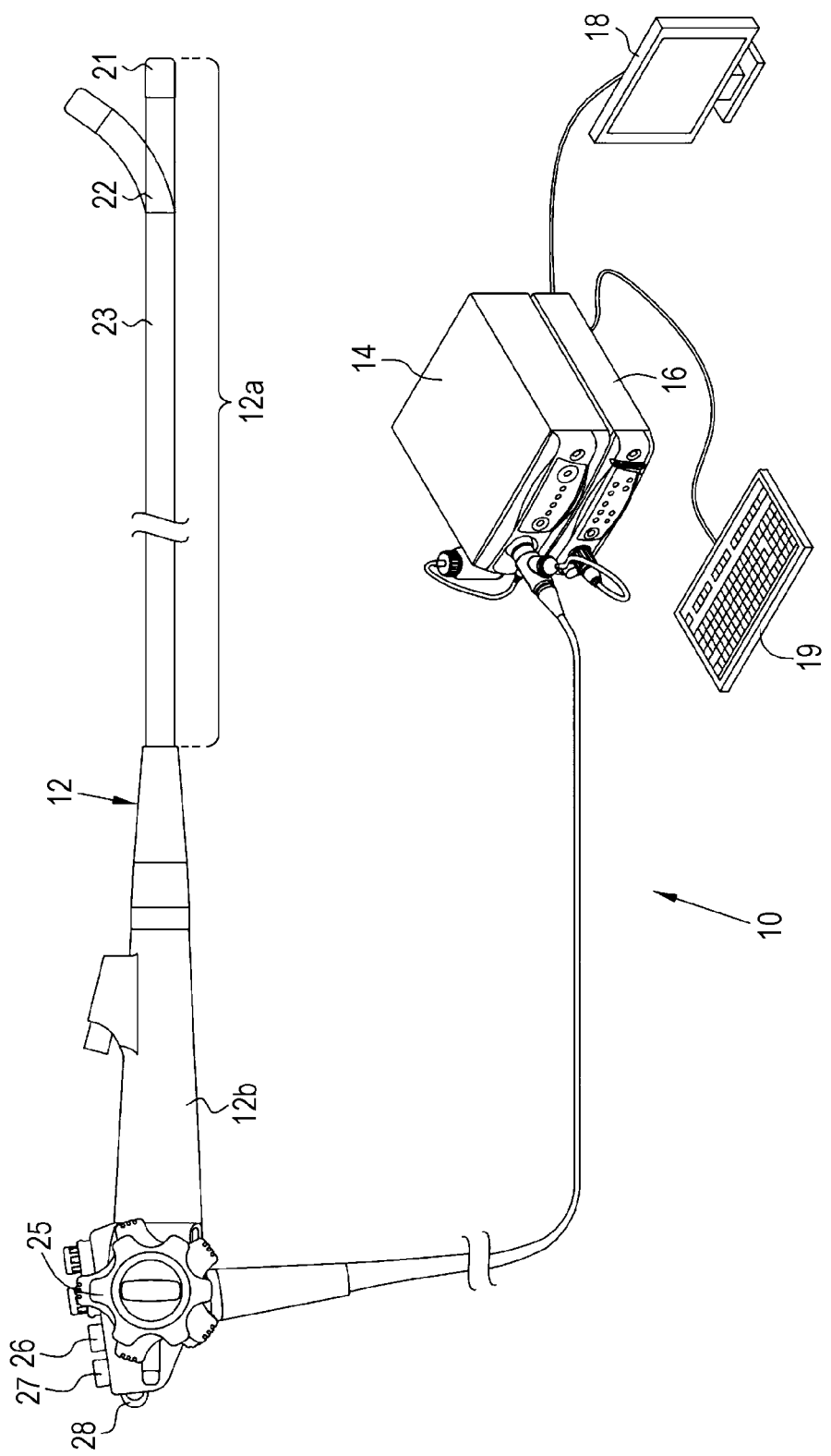
FIG. 1 is an external view of an endoscope system according to a first embodiment.

As illustrated in FIG. 1, an endoscope system 10 has an endoscope 12, a light source device 14, a processor device 16, a display unit 18, and an instruction input part 19. The endoscope 12 image-captures an observation portion in a living body serving as a subject. The light source device 14 supplies illumination light that illuminates the observation portion, to the endoscope 12. The processor device 16 generates a display image of the observation portion by using an image pick-up signal obtained by image-capturing. The display unit 18 is a monitor that displays a display image and information and so forth accompanying the display image. The instruction input part 19 is a console of a keyboard, a mouse, and so forth, and functions as a user interface that receives input operations, such as designation of a region of interest (ROI) and functional setting. The display unit 18 and the instruction input part 19 are electrically connected to the processor device 16.

The endoscope 12 is optically connected to the light source device 14, and is electrically connected to the processor device 16. The endoscope 12 has an insertion section 12a and an operation section 12b.

The insertion section 12a is a section that is inserted into an alimentary canal or the like of the living body. The insertion section 12a has a distal end portion 21, a bending portion 22, and a flexible pipe portion 23 that are coupled in that order from the distal end side. The distal end portion 21 has, at a distal end surface, an illumination window, an observation window, an air/water supply nozzle, and a forceps port (none of these is illustrated). The illumination window is for irradiating the observation portion with the illumination light. The observation window is for taking in the light from the observation portion. The air/water supply nozzle is for washing the illumination window and the observation window. The forceps port is for performing various treatments using treatment tools, such as a pair of forceps and an electric scalpel. The bending portion 22 is constituted by coupling a plurality of bending pieces, and bends in up-down and left-right directions. The flexible pipe portion 23 is flexible, and can be inserted into a bending tubular path, such as the esophagus or intestine.

The operation section 12b has an angle knob 25, an image storage operating unit 26, a mode switching unit 27, and a zoom operating unit 28. The angle knob 25 is used for an operation of bending the bending portion 22 so as to direct the distal end portion 21 in a desirable direction. The image storage operating unit 26 is used for an operation of storing a still image and/or a movie in a storage (not illustrated). The mode switching unit 27 is used for an operation of switching an observation mode. The zoom operating unit 28 is used for an operation of changing zoom magnification.

The endoscope system 10 has, as operation modes, a normal observation mode, a special observation mode, and an imaging condition guidance mode. In the normal observation mode, an image in which an observation object with natural colors is captured (hereinafter, referred to as normal observation image) is acquired. In the special observation mode, an image in which a blood vessel that is an observation object is at least emphasized (hereinafter, referred to as special observation image) is acquired.

Although specifically described later, in the imaging condition guidance mode, an image in which a structure of an observation object is emphasized (structure emphasis image) is acquired, the structure emphasis image being emphasized by using a first index value acquirable under a first imaging condition acquired by an imaging condition acquisition unit 70. In addition, in the imaging condition guidance mode, guidance of a second imaging condition for acquiring a second index value non-acquirable under the first imaging condition is displayed. In this embodiment, a structure includes a structure of a blood vessel and a structure of a gland duct (pit pattern). In the following description, when a structure of a blood vessel and a structure of a gland duct are not distinguished from each other, these structures each are referred to as a structure.

Figure 2:
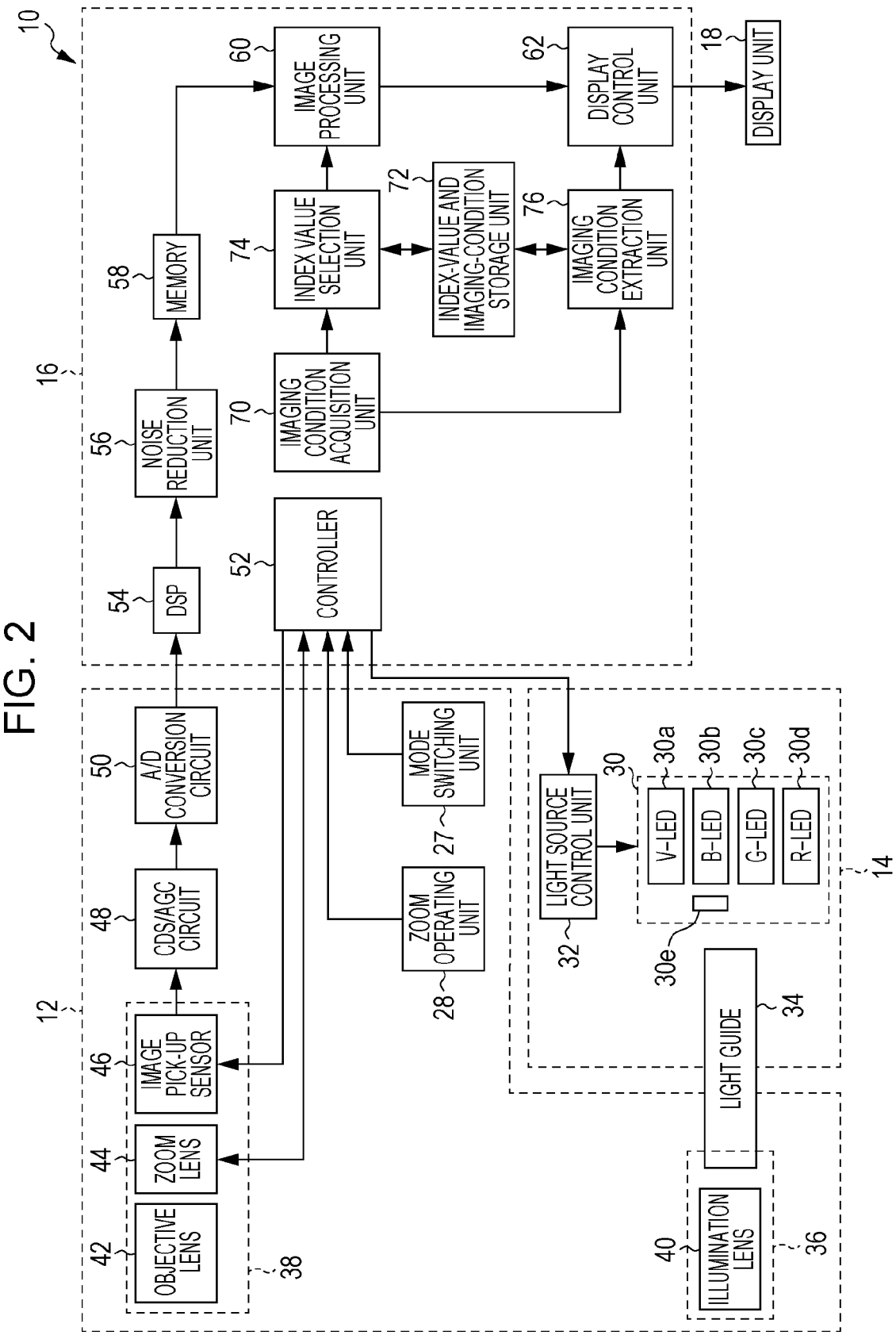
FIG. 2 is a block diagram illustrating a function of the endoscope system.

As illustrated in FIG. 2, the light source device 14 includes a light source 30 that emits illumination light, and a light source control unit 32 that controls the light source 30. The light source 30 is, for example, a semiconductor light source such as light emitting diodes (LEDs) of a plurality of colors with different wavelength ranges.

In this embodiment, the light source 30 has, for example, four-color LEDs of a violet light emitting diode (V-LED) 30a, a blue light emitting diode (B-LED) 30b, a green light emitting diode (G-LED) 30c, and a red light emitting diode (R-LED) 30d. The V-LED 30a emits light with light emission wavelengths in a range of from 380 nm to 420 nm. The B-LED 30b emits light with light emission wavelengths in a range of from 420 nm to 500 nm. The G-LED 30c emits light with light emission wavelengths in a range of from 480 nm to 600 nm. The R-LED 30d emits light with light emission wavelengths in a range of from 600 nm to 650 nm. The lights of the respective colors may each have the same central wavelength and peak wavelength, or may have different central wavelength and peak wavelength.

The light source 30 includes an optical filter 30e that adjusts the wavelength range of light emitted from a LED. In this embodiment, the optical filter 30e is arranged on the optical path of the B-LED 30b, and transmits a short wavelength component included in the wavelength range of the B-LED 30b. To be specific, the optical filter 30e transmits light of 450 nm or shorter included in the wavelength range of the B-LED 30b. A long wavelength component included in the wavelength range of the B-LED 30b decreases the contrast between a mucous membrane and a blood vessel. Thus, by using the optical filter 30e, the short wavelength component included in the wavelength range of the B-LED 30b is supplied to a light guide 34 (described later). The optical filter 30e is arranged on the optical path of the B-LED 30b in this embodiment; however, it is not limited thereto. For example, the optical filter 30e may be arranged on the optical path of the G-LED 30c. The wavelength component to be transmitted by the optical filter 30e can be appropriately set. For example, when the optical filter 30e is arranged on the optical path of the G-LED 30c, the optical filter 30e transmits part of the wavelength range of the G-LED 30c.

The light source control unit 32 adjusts the light emitting timing, light emitting duration, light quantity, and spectrum of illumination light of each of the LEDs 30a to 30d by independently controlling turning ON and OFF of each of the LEDs 30a to 30d, and the balance of respective emission light quantities of the LEDs 30a to 30d (hereinafter, referred to as light quantity ratio). In this embodiment, the light source control unit 32 controls the light quantity ratio of the LEDs 30a to 30d on an observation mode basis by adjusting the electric current and voltage for driving each of the LEDs 30a to 30d.

Figure 3:
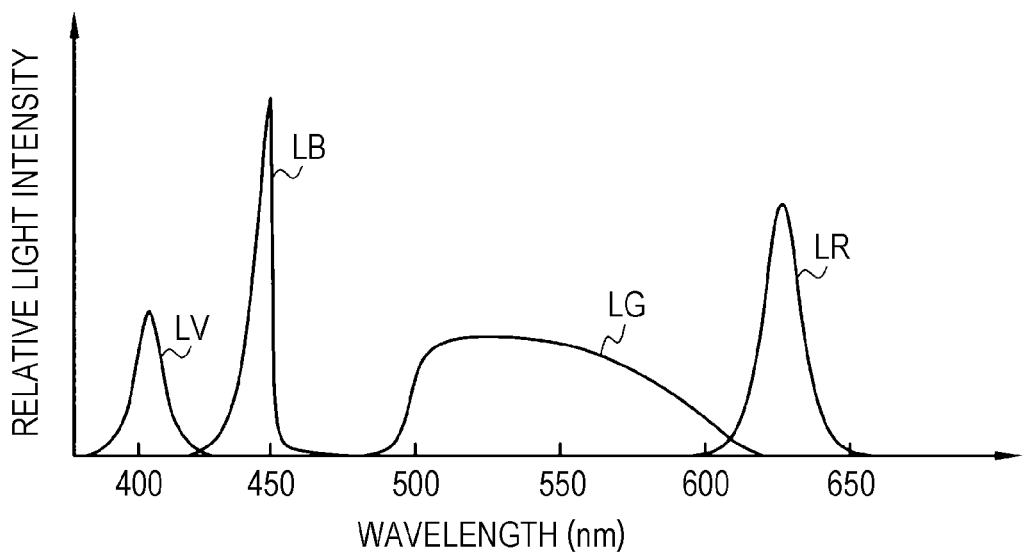
FIG. 3 illustrates a light intensity spectrum of illumination light in a normal observation mode.

As illustrated in FIG. 3, in the normal observation mode, the light source control unit 32 turns ON all the LEDs 30a to 30d, and hence almost white illumination light (hereinafter, referred to as white light) including violet light LV emitted from the V-LED 30a, blue light LB emitted from the B-LED 30b, green light LG emitted from the G-LED 30c, and red light LR emitted from the R-LED 30d is emitted. In this embodiment, the blue light LB is light transmitted through the optical filter 30e, that is, light of 450 nm or shorter included in the wavelength range of the B-LED 30b.

Figure 4:
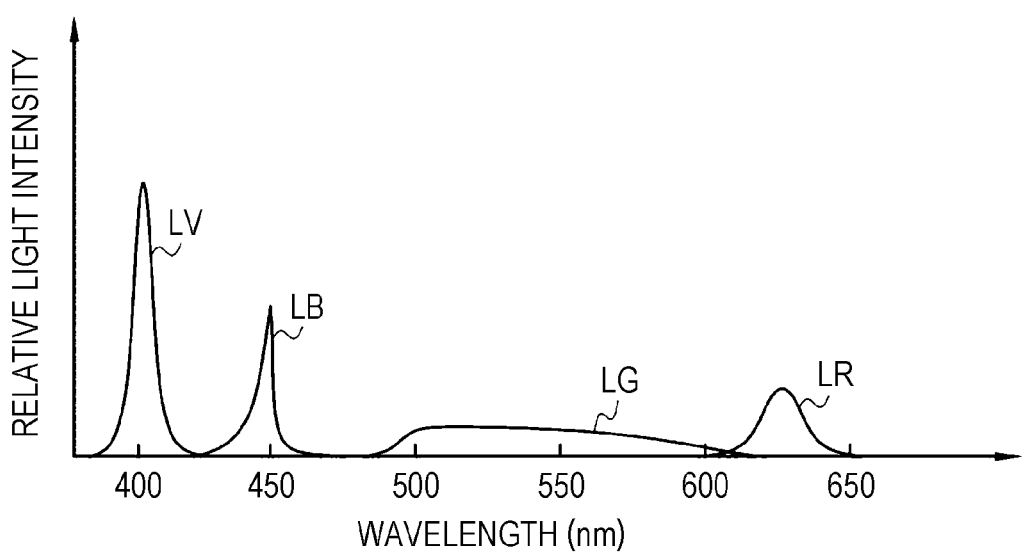
FIG. 4 illustrates a light intensity spectrum of illumination light in a special observation mode.

As illustrated in FIG. 4, in the special observation mode, the light source control unit 32 causes illumination light to be emitted such that the emission light quantity of the V-LED 30a is larger than that in the normal observation mode and the respective emission light quantities of the B-LED 30b, G-LED 30c, and R-LED 30d are smaller than those in the normal observation mode.

In the case of the imaging condition guidance mode, the light source control unit 32 controls light emission of the LEDs 30a to 30d in accordance with the light quantity ratio input by the instruction input part 19. For example, when the light quantity ratio is (the emission light quantity of the V-LED 30*a*):(the emission light quantity of the B-LED 30*b*):(the emission light quantity of the G-LED 30*c*):(the emission light quantity of the R-LED 30*d*), and when the light quantity ratio input by the instruction input part 19 is 1:0:0:0, the light source control unit 32 turns ON only the V-LED 30*a* among the LEDs 30*a* to 30*d*, and hence the violet light LV is emitted. The violet light LV is light in a wavelength range that is optimal for observing a surface layer blood vessel located at a shallow position from a mucous membrane surface. When the light quantity ratio input by the instruction input part 19 is 0:1:0:0, the light source control unit 32 turns ON only the B-LED 30*b* among the LEDs 30*a* to 30*d*, and hence the blue light LB is emitted. The blue light LB is light in a wavelength range that is optimal for observing a middle layer blood vessel located at a position deeper than the position of a surface layer blood vessel. In this embodiment, the blue light LB is emitted in the imaging condition guidance mode.

The illumination light emitted from the light source 30 is incident on the light guide 34 inserted through the insertion section 12*a*. The light guide 34 is embedded in the endoscope 12 and a universal cord. Illumination light propagates through the light guide 34 to the distal end portion 21 of the endoscope 12. The universal cord is a cord that connects the endoscope 12, the light source device 14, and the processor device 16 to one another. For the light guide 34, a multi-mode fiber can be used. For example, for the light guide 34, a small-diameter fiber cable having a core diameter of 105 μm, a cladding diameter of 125 μm, and a diameter including a protective layer serving as an outer cover in a range of from φ0.3 to 0.5 mm can be used.

The distal end portion 21 has an illumination optical system 36 and an image pick-up optical system 38. The illumination optical system 36 has an illumination lens 40. The illumination light propagating through the light guide 34 illuminates an observation object via the illumination lens 40. The image pick-up optical system 38 has an objective lens 42, a zoom lens 44, and an image pick-up sensor 46. Various lights, such as reflected light, scattered light, and fluorescence, from the observation object are incident on the image pick-up sensor 46 via the objective lens 42 and the zoom lens 44. Thus, an image of the observation object is formed on the image pick-up sensor 46. The zoom lens 44 freely moves between the telephoto end and the wide end by operating the zoom operating unit 28, to enlarge or contract the image of the observation object formed on the image pick-up sensor 46.

The image pick-up sensor 46 is a color image pick-up sensor provided with a color filter of one of primary colors of red (R), green (G), and blue (B) for each pixel, image-captures the observation object, and outputs an image signal of corresponding one of RGB. For the image pick-up sensor 46, a charge coupled device (CCD) image pick-up sensor, a complementary metal-oxide semiconductor (CMOS) image pick-up sensor, or the like, can be used. Alternatively, instead of the image pick-up sensor 46 provided with the color filters of the primary colors, a complementary-color image pick-up sensor including complementary-color filters of cyan (C), magenta (M), yellow (Y), and green (G) may be used. When the complementary-color image pick-up sensor is used, image signals of four colors of CMYG are output. By converting the image signals of the four colors of CMYG into the image signals of the three colors of RGB by color conversion from complementary colors to primary colors, image signals of the respective colors of RGB similar to those of the image pick-up sensor 46 can be obtained.

Instead of the image pick-up sensor 46, a monochrome sensor without a color filter may be used.

A correlated double sampling (CDS)/automatic gain control (AGC) circuit 48 performs correlative double sampling and automatic gain control on an analog image signal output from the image pick-up sensor 46. An analog to digital (A/D) conversion circuit 50 converts the analog image signal output from the CDS/AGC circuit 48 into a digital image signal. The A/D conversion circuit 50 inputs the digital image signal after the A/D conversion to the processor device 16.

The processor device 16 includes a controller 52, a digital signal processor (DSP) 54, a noise reduction unit 56, a memory 58, an image processing unit 60, and a display control unit 62.

The controller 52 has a central processing unit (CPU), a read only memory (ROM) that stores a control program and setting data required for the control, and a random access memory (RAM) serving as a work memory that loads the control program. When the CPU executes the control program, the controller 52 controls respective units of the processor device 16, and the light source control unit 32 and the image pick-up sensor 46. The respective units of the processor device 16 each may be composed of a programmable logic device (PLD) that is a processor whose circuit configuration is changeable after manufacturing, such as a field programmable gate array (FPGA); or a dedicated electric circuit having a circuit configuration designed dedicatedly for executing specific processing, such as an application specific integrated circuit (ASIC). The above configuration can be similarly applied to the inside portions of the endoscope 12 and the light source device 14.

The DSP 54 acquires the digital image signal from the endoscope 12, and performs various signal processing on the acquired image signal, for example, defect correction processing, offset processing, gain correction processing, linear matrix processing, gamma conversion processing, and demosaicing processing. The defect correction processing corrects a signal of a defect pixel of the image pick-up sensor 46. The offset processing removes a dark current component from the image signal after the defect correction processing and sets an accurate zero level. The gain correction processing adjusts the signal level by multiplying the image signal after the offset processing, by a specific gain.

The linear matrix processing increases the color reproducibility of the image signal after the gain correction processing. The gamma conversion processing adjusts the brightness and color saturation of the image signal after the linear matrix processing. By performing demosaicing processing (also referred to as isotropy processing) on the image signal after the gamma conversion processing, a signal of an insufficient color of each pixel is generated through interpolation. With the demosaicing processing, all pixels have signals of the respective colors of RGB.

The noise reduction unit 56 performs noise reduction processing by, for example, a moving average method or a median filter method, on the image signal after the demosaicing processing by the DSP 54 to reduce noise. The image signal after the noise reduction is stored in the memory 58.

The image processing unit 60 acquires the image signal from the memory 58, performs predetermined image processing on the acquired image signal, and generates a display image in which the observation object is captured. The content of image processing that is performed by the image processing unit 60 varies on an observation mode basis.

In the normal observation mode, the image processing unit 60 performs image processing, such as color conversion processing, chromatic emphasis processing, and structure emphasis processing, and generates a normal observation image. The color conversion processing is processing for performing color conversion on the image signal through 3×3 matrix processing, gradation transformation processing, and three-dimensional look-up table (LUT) processing. The chromatic emphasis processing is performed on the image signal after the color conversion processing. The structure emphasis processing is processing for emphasizing a specific tissue or structure included in an observation object, such as a blood vessel or a gland duct, and is performed on the image signal after the chromatic emphasis processing. In the special observation mode, the image processing unit 60 performs the above-described various image processing for emphasizing the blood vessel and hence generates a special observation image. In the special observation mode, the emission light quantity of the V-LED 30*a* is large. Thus, in the special observation image, a surface layer blood vessel is emphasized.

Figure 5:
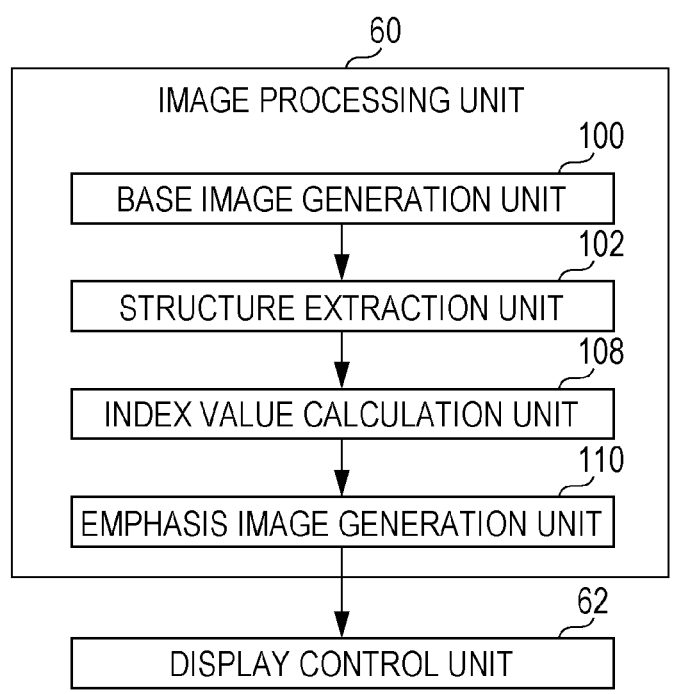
FIG. 5 is a block diagram explaining an image processing unit.

As illustrated in FIG. 5, the image processing unit 60 has a base image generation unit 100, a structure extraction unit 102, an index value calculation unit 108, and an emphasis image generation unit 110. In the imaging condition guidance mode, the image processing unit 60 performs various image processing by using the above-described respective units.

The base image generation unit 100 generates a base image, in which a structure of an observation object is expressed by using a difference in color, from an image signal acquired from the memory 58, and acquires the generated base image as an endoscope image. That is, the base image generation unit 100 acquires an endoscope image obtained by an endoscope image-capturing an observation object. The base image is expressed with a hue corresponding to the set light quantity ratio, and the hue is slightly different from that of a normal observation image. An example of the base image may be an image with a color balance that a white plate in an image obtained by imaging with the set light quantity ratio appears white; a gray image obtained by assigning an image signal to one of an R channel, a G channel, and a B channel of the display unit 18 (for example, when the light quantity of the green light LG is large in a light quantity ratio of illumination light; an image signal is assigned to the G channel); an image with a pseudo color obtained by changing the gradation balance of an image signal and assigning the image signal to one of the channels; and other images. The base image generation unit 100 corresponds to an image acquisition unit of the present invention.

The structure extraction unit 102 generates a structure extraction image by extracting the structure of the observation object from the base image. For example, when the light source device 14 illuminates the observation object with illumination lights in different wavelength ranges, the structure extraction unit 102 extracts a blood vessel by taking a difference between images obtained by imaging the observation object illuminated with the respective illumination lights. To be specific, by taking a difference between an image obtained by imaging the observation object illuminated with the violet light LV and an image obtained by imaging the observation object illuminated with the blue light LB, a surface layer blood vessel or a blood vessel located at a shallower position than the position of the surface layer blood vessel can be extracted. In addition to or instead of extracting the blood vessel as described above, a structure of a gland duct may be extracted. The method of extracting a structure is not limited to the above-described method. In addition, while the structure extraction unit 102 extracts a blood vessel and a gland duct from the entirety of a base image in this embodiment, when a region of interest is designated through an operation with the instruction input part 19, a blood vessel and a gland duct may be extracted within only the designated region of interest.

The index value calculation unit 108 uses the structure extraction image and calculates an index value relating to a structure of an observation object. The types of index values are, for example, the density of a blood vessel, the uniformity of the thickness of a blood vessel, the complexity of a blood vessel, and the uniformity of a surface structure. The types of index values are not limited to the above-described example. The density of a blood vessel is the proportion of a blood vessel per unit area. The uniformity of the thickness of a blood vessel is an index value relating to a variation in the thickness of a blood vessel. The complexity of a blood vessel is an index value indicating the degree of complexity of the shape of a blood vessel. For example, the complexity of a blood vessel is a value calculated by combining the number of branch points of an extracted blood vessel (branch number), the degree of meandering of the blood vessel, the degree of curve of the extracted blood vessel (curvature), and so forth. The uniformity of a surface structure is an index value relating to a variation in the shape of a gland duct. In this embodiment, the index value calculation unit 108 calculates an index value selected by an index value selection unit 74 (described later) among the above-described plurality of index values.

The index value calculation unit 108 calculates an index value for each pixel of the structure extraction image. For example, the index value calculation unit 108 calculates an index value of a single pixel by using data of pixels within a predetermined range including the pixels for which the index value is to be calculated (for example, a range of 99×99 pixels around the pixels for which the index value is to be calculated).

When a region of interest is set in part of the structure extraction image through an operation with the instruction input part 19, the index value calculation unit 108 calculates an index value within the set region of interest. When a region of interest is not set or when a region of interest is set for the entirety of the structure extraction image, the index value calculation unit 108 calculates an index value for the entirety of the structure extraction image.

While the index value calculation unit 108 calculates an index value by using a structure extraction image in this embodiment, the index value calculation unit 108 may calculate an index value by using an endoscope image acquired by the base image generation unit 100 serving as the image acquisition unit. For example, when a structure of an observation object clearly appears in an endoscope image, an index value is calculated by using this endoscope image.

The emphasis image generation unit 110 uses the generated base image and the calculated index value, and generates a structure emphasis image serving as a first structure emphasis image. The emphasis image generation unit 110 generates a structure emphasis image, for example, by performing overlap processing of overlaying information based on the index value, on the base image. The overlap processing may be coloring processing corresponding to the index value. In the structure emphasis image after the coloring processing, a region with an index value that is a certain value or larger is displayed with a pseudo color and the structure of the observation object is emphasized as compared with the base image. In this case, information indicating the value of the index value may be overlaid on the base image. The emphasis image generation unit 110 inputs the generated structure emphasis image to the display control unit 62. The emphasis image generation unit 110 corresponds to a first emphasis image generation unit of the present invention.

The display control unit 62 controls the display unit 18 to display the display image generated by the image processing unit 60. Thus, the normal observation image is displayed in the normal observation mode, and the special observation image is displayed in the special observation mode. In the imaging condition guidance mode, the structure emphasis image is displayed and the guidance is displayed.

Next, the imaging condition guidance mode is described in detail. The processor device 16 further has an imaging condition acquisition unit 70, an index-value and imaging-condition storage unit 72, an index value selection unit 74, and an imaging condition extraction unit 76 (see FIG. 2). The index-value and imaging-condition storage unit 72 is composed of a recording medium, such as a hard disc drive (HDD) or a solid state drive (SSD).

The imaging condition acquisition unit 70 acquires a first imaging condition as an imaging condition for imaging an observation object by using the endoscope 12. The first imaging condition includes at least one of the light quantity ratio of the LEDs 30a to 30d, the observation distance with respect to the observation object, or the zoom magnification of the endoscope 12. The light quantity ratio is acquired from the light source control unit 32. The observation distance may be, for example, a non-enlarged observation distance that the observation distance is a long distance, and an enlarged observation distance that the observation distance is a short distance. The observation distance is acquired in accordance with the exposure light quantity obtained from an image. In this case, the observation distance may be acquired through frequency analysis of an image. The zoom magnification may be, for example, non-enlargement for non-enlarged observation, and a value from a low magnification to a high magnification enabling enlarged observation. The zoom magnification is acquired on the basis of a change operation of the zoom operating unit 28. In this embodiment, the imaging condition acquisition unit 70 acquires the light quantity ratio, the observation distance, and the zoom magnification, as the first imaging condition. The imaging condition acquisition unit 70 inputs the acquired first imaging condition to the index value selection unit 74 and the imaging condition extraction unit 76.

The index-value and imaging-condition storage unit 72 stores a plurality of imaging conditions, and an acquirable index value and a non-acquirable index value under each of the imaging conditions in an associated manner. An index value non-acquirable under a certain imaging condition includes an index value that is theoretically non-acquirable, and an index value that is theoretically acquirable but that cannot be calculated, from an image, with a certain degree or higher of accuracy useful for the diagnosis purpose. In this embodiment, the index-value and imaging-condition storage unit 72 stores the light quantity ratio, the observation distance, and the zoom magnification as imaging conditions. The imaging conditions stored in the index-value and imaging-condition storage unit 72 include at least the first imaging condition acquired by the imaging condition acquisition unit 70. That is, the index-value and imaging-condition storage unit 72 stores correspondence between the imaging condition, and a plurality of index values including a first index value acquirable under the first imaging condition and a second index value non-acquirable under the first imaging condition but acquirable under a second imaging condition. While the imaging condition stored in the index-value and imaging-condition storage unit 72 is the light quantity ratio, the observation distance, and the zoom magnification in this embodiment, it is not limited thereto. For example, the imaging conditions may include an observation mode (the normal observation mode, the special observation mode, etc.), the light emission quantity of the light source 30, brightness of the entirety or part (region of interest etc.) of the display screen, and so forth. In addition, the light quantity ratio as the imaging condition may include the light quantity ratio of the normal observation mode and the light quantity ratio of the special observation mode.

As illustrated in FIG. 6, in the index-value and imaging-condition storage unit 72, for example, an imaging condition C11 and an imaging condition C12 among the plurality of imaging conditions are associated with different index values. Regarding the imaging condition C11, the light quantity ratio is R11, the observation distance is an enlarged observation distance, and the zoom magnification is a low magnification. The index values acquirable under the imaging condition C11 are the density of a middle layer blood vessel, the complexity of a middle layer blood vessel, and the uniformity of the thickness of a middle layer blood vessel. The index values non-acquirable under the imaging condition C11 are the density of a surface layer blood vessel, the complexity of a surface layer blood vessel, and the uniformity of a surface layer structure. The light quantity ratio R11 is, for example, 0:1:0:0. Thus, with the light quantity ratio R11, blue light LB is emitted as illumination light.

Regarding the imaging condition C12, the light quantity ratio is R12, the observation distance is an enlarged observation distance, and the zoom magnification is a low magnification. The index values acquirable under the imaging condition C12 are the density of a surface layer blood vessel, the complexity of a surface layer blood vessel, and the uniformity of a surface layer structure. The index values non-acquirable under the imaging condition C12 are the density of a middle layer blood vessel, the complexity of a middle layer blood vessel, and the uniformity of the thickness of a middle layer blood vessel. The light quantity ratio R12 is, for example, 1:0:0:0. Thus, with the light quantity ratio R12, violet light LV is emitted as illumination light.

The index value selection unit 74 uses the first imaging condition acquired by the imaging condition acquisition unit 70, refers to the index-value and imaging-condition storage unit 72, and selects the first index value.

Figure 7:
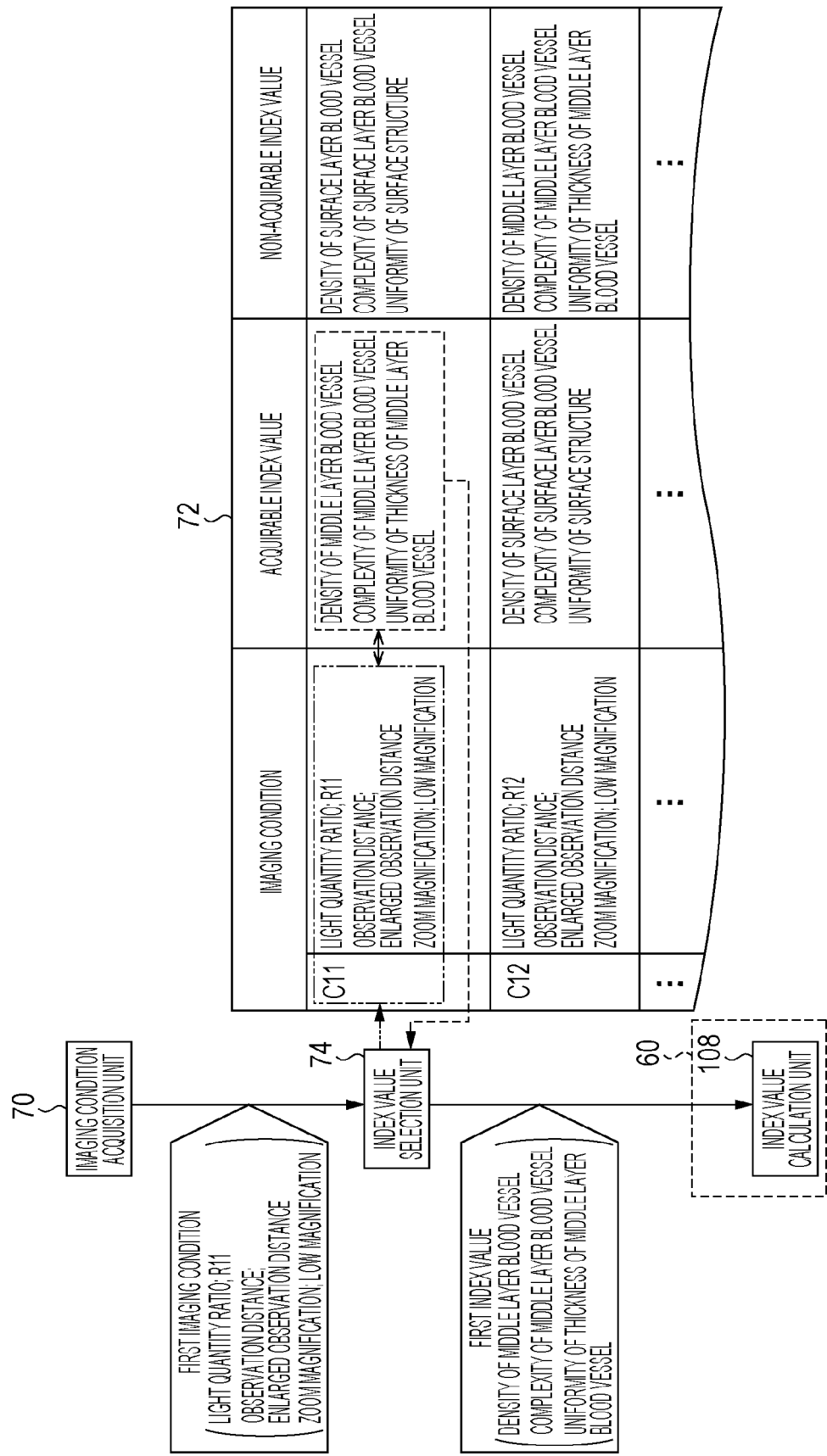
FIG. 7 is an illustration explaining an index value selection unit.

As illustrated in FIG. 7, for example, as the first imaging condition, when the light quantity ratio is R11, the observation distance is an enlarged observation distance, and the zoom magnification is a low magnification, the index value selection unit 74 extracts the imaging condition C11 that meets the first imaging condition from among the plurality of imaging conditions stored in the index-value and imaging-condition storage unit 72. The index value selection unit 74 selects, as the first index value acquirable under the extracted imaging condition C11, the density of a middle layer blood vessel, the complexity of a middle layer blood vessel, and the uniformity of the thickness of a middle layer blood vessel. The index value selection unit 74 inputs the selected first index value to the index value calculation unit 108 of the image processing unit 60.

The imaging condition extraction unit 76 uses the first imaging condition acquired by the imaging condition acquisition unit 70, refers to the index-value and imaging-condition storage unit 72, and extracts the second imaging condition under which the second index value is acquirable.

Figure 8:
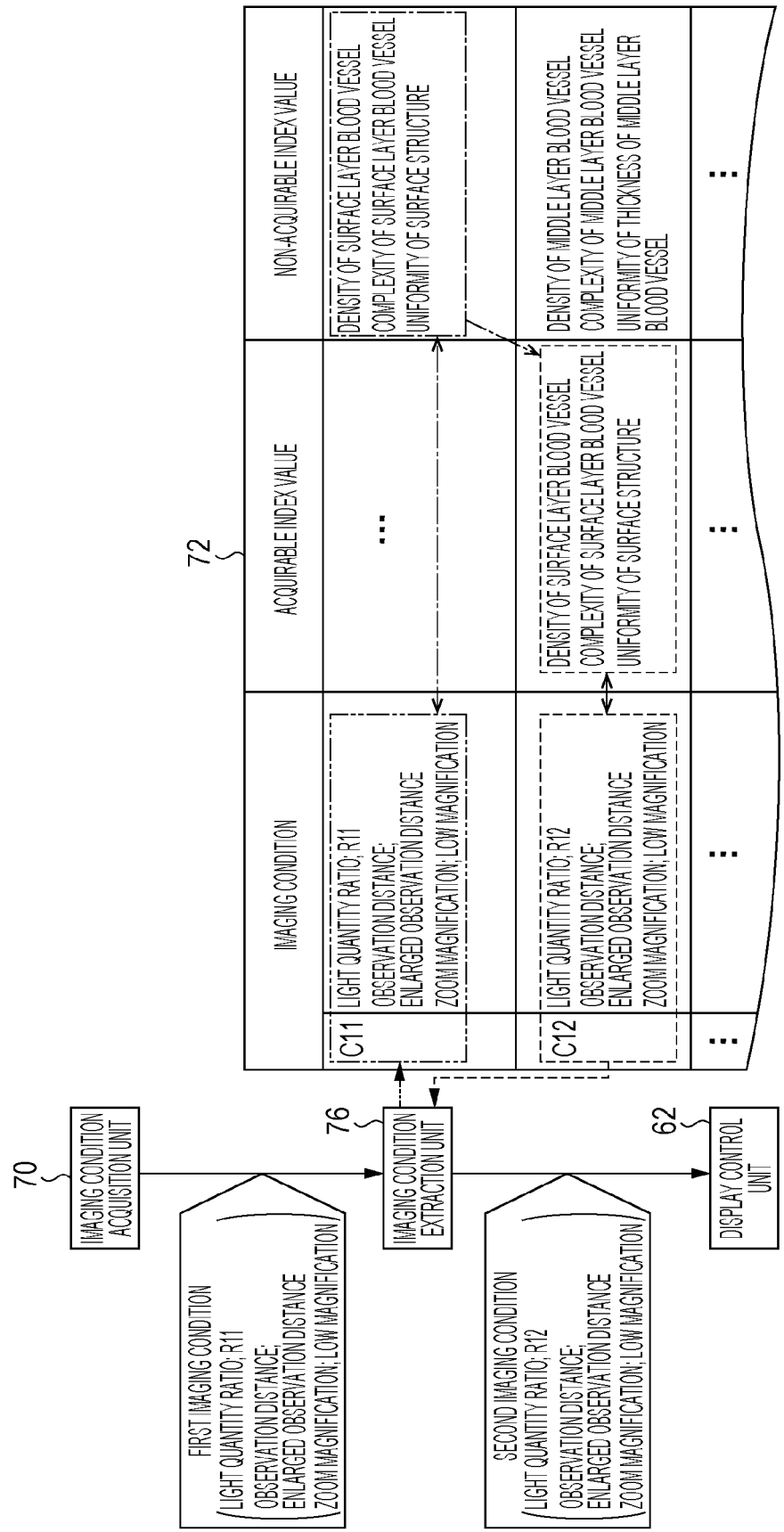
FIG. 8 is an illustration explaining an imaging condition extraction unit.

As illustrated in FIG. 8, the imaging condition extraction unit 76 first extracts the imaging condition C11 that meets the first imaging condition from among the plurality of imaging conditions stored in the index-value and imaging-condition storage unit 72. The imaging condition extraction unit 76 selects, as the second index value acquirable under the extracted imaging condition C11, the density of a surface layer blood vessel, the complexity of a surface layer blood vessel, and the uniformity of a surface structure. The imaging condition extraction unit 76 extracts, as the second imaging condition, the imaging condition C12 (the light quantity ratio is R12, the observation distance is an enlarged observation distance, the zoom magnification is a low magnification) under which the selected second index value is acquirable from among the plurality of imaging conditions. The imaging condition extraction unit 76 inputs the extracted second imaging condition to the display control unit 62. In the imaging condition guidance mode, the display control unit 62 controls the display unit 18 to display guidance indicating that the second index value is acquirable under the second imaging condition extracted by the imaging condition extraction unit 76. Thus, the display unit 18 corresponds to a guidance display unit of the present invention.

Figure 9:
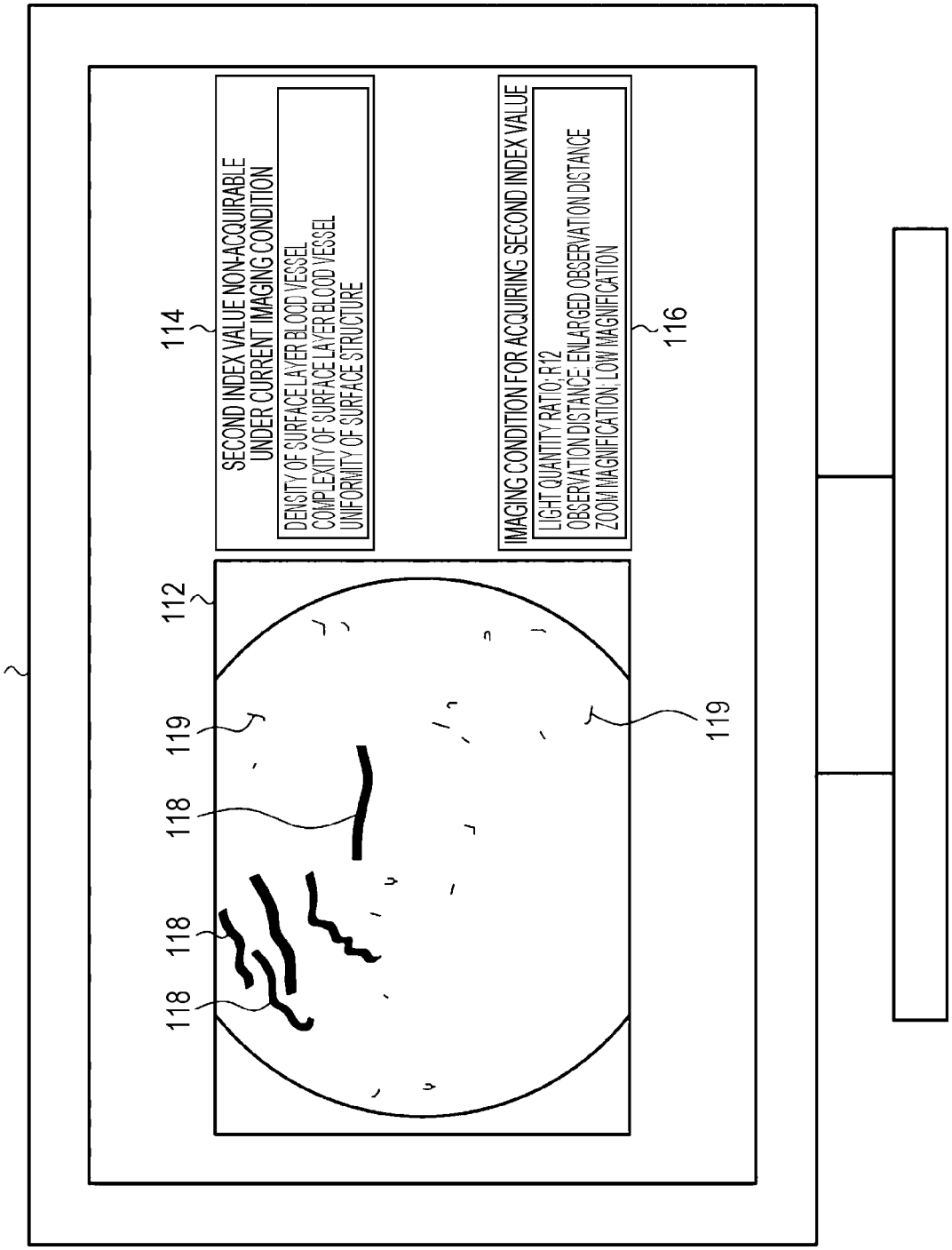
FIG. 9 illustrates a display screen of a display unit.

As illustrated in FIG. 9, for example, the display control unit 62 controls the display unit 18 to display a structure emphasis image 112, information 114 indicating the second index value non-acquirable under the current first imaging condition, and information 116 indicating the second imaging condition for acquiring the second index value. The structure emphasis image 112 is displayed in a left region of the display unit 18. The information 114 indicating the second index value non-acquirable under the first imaging condition is displayed in an upper right region of the display unit 18. The information 116 indicating the second imaging condition for acquiring the second index value is displayed in a lower right region of the display unit 18.

In the structure emphasis image 112, for example, a region 118 having a complexity of a middle layer blood vessel being a certain value or larger is displayed with a pseudo color. The region 118 has, for example, a red-based color. In the structure emphasis image 112, since the region 118 is displayed in an emphasized manner in this way, the complexity and so forth of a middle layer blood vessel is easily recognized.

The structure emphasis image 112 is an image using blue light LB as illumination light. A middle layer blood vessel is clearly captured whereas a surface layer blood vessel 119 is not clear as compared with the middle layer blood vessel. Thus, the index value relating to the middle layer blood vessel can be correctly acquired from the structure emphasis image 112 acquired under the first imaging condition; however, it is difficult to correctly acquire the index value relating to the surface layer blood vessel 119. Further, since the shape of a gland duct is not clearly captured, it is also difficult to acquire the uniformity of a surface structure. As the information 114 indicating the second index value non-acquirable under the first imaging condition, "the density of a surface layer blood vessel, the complexity of a surface layer blood vessel, and the uniformity of a surface structure" are displayed. Further, as the information 116 indicating the second imaging condition for acquiring the second index value, "the light quantity ratio being R12, the observation distance being an enlarged observation distance, and the zoom magnification being a low magnification" are displayed.

Figure 10:
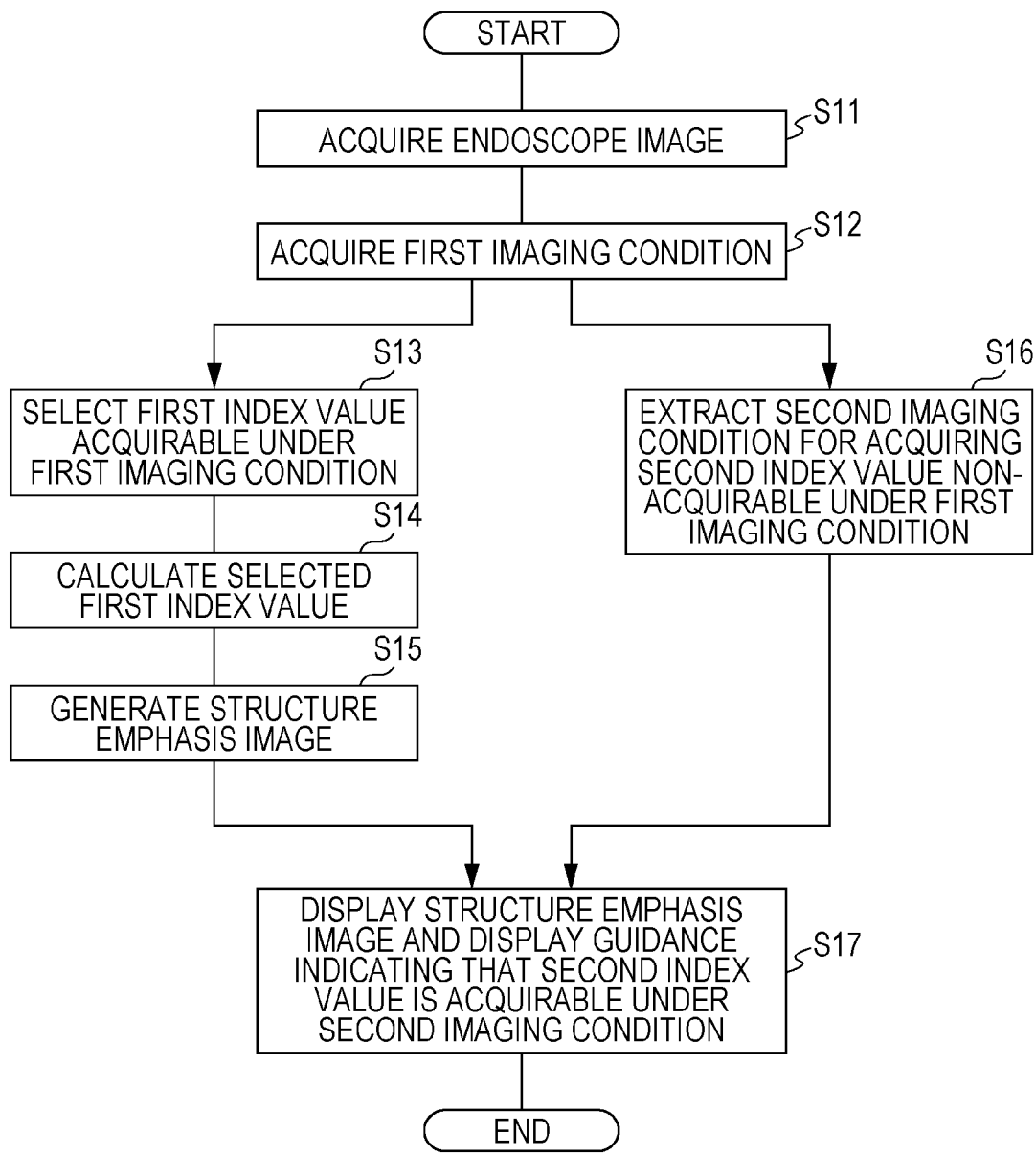
FIG. 10 is a flowchart explaining an operation in a suitable object observation mode of the endoscope system.

Next, an operation of the imaging condition guidance mode is described with reference to a flowchart in FIG. 10.

In the imaging condition guidance mode, illumination light is emitted in accordance with the light quantity ratio input by the instruction input part 19. To be specific, only the B-LED 30b is turned ON among the LEDs 30a to 30d, and hence blue light LB is emitted. With the illumination light, an observation object in illumination is imaged by the image pick-up sensor 46. The base image generation unit 100 generates a base image from an image signal output from the image pick-up sensor 46, and acquires the generated base image as an endoscope image (S11). The structure extraction unit 102 generates a structure extraction image by extracting a structure of the observation object from the base image.

The imaging condition acquisition unit 70 acquires the first imaging condition as an imaging condition for performing the imaging (S12). The first imaging condition acquired by the imaging condition acquisition unit 70 includes the light quantity ratio of the LEDs 30a to 30d, the observation distance with respect to the observation object, and the zoom magnification of the endoscope 12. The imaging condition acquisition unit 70 inputs the acquired first imaging condition to the index value selection unit 74 and the imaging condition extraction unit 76.

The index value selection unit 74 refers to the index-value and imaging-condition storage unit 72 and selects the first index value acquirable under the first imaging condition acquired by the imaging condition acquisition unit 70 (S13). The index-value and imaging-condition storage unit 72 stores correspondence between an imaging condition, and a plurality of index values including the first index value acquirable under the first imaging condition and the second index value non-acquirable under the first imaging condition but acquirable under the second imaging condition. The index value selection unit 74 extracts the imaging condition that meets the acquired first imaging condition from the index-value and imaging-condition storage unit 72. The index value selection unit 74 selects the first index value associated with the extracted imaging condition. The index value selection unit 74 inputs the selected first index value to the index value calculation unit 108.

The index value calculation unit 108 uses the structure extraction image and calculates the first index value selected by the index value selection unit 74 (S14). The emphasis image generation unit 110 uses the calculated first index value and the base image, and generates a structure emphasis image (S15). The emphasis image generation unit 110 inputs the generated structure emphasis image to the display control unit 62.

The imaging condition extraction unit 76 refers to the index-value and imaging-condition storage unit 72 and extracts the second imaging condition for acquiring the second index value non-acquirable under the first imaging condition (S16). To be specific, the imaging condition extraction unit 76 extracts the imaging condition that meets the first imaging condition from the index-value and imaging-condition storage unit 72. The imaging condition extraction unit 76 selects the second index value associated with the extracted imaging condition. The imaging condition extraction unit 76 extracts, as the second imaging condition, the imaging condition under which the selected second index value is acquirable from among the plurality of imaging conditions. The imaging condition extraction unit 76 inputs the extracted second imaging condition to the display control unit 62.

The display control unit 62 controls the display unit 18 to display the structure emphasis image generated by the emphasis image generation unit 110, and to display the guidance indicating that the second index value is acquirable under the second imaging condition extracted by the imaging condition extraction unit 76 (S17).

By displaying the guidance of the imaging condition for acquiring the second index value non-acquirable under the current imaging condition, the index value non-acquirable under the current imaging condition can be acquired.

In the above-described first embodiment, the display control unit 62 provides the guidance display indicating that the second index value is acquirable under the second imaging condition extracted by the imaging condition extraction unit 76. In addition to this, the display control unit 62 may provide guidance display indicating that the first index value is acquirable under the first imaging condition acquired by the imaging condition acquisition unit 70.

Figure 11:
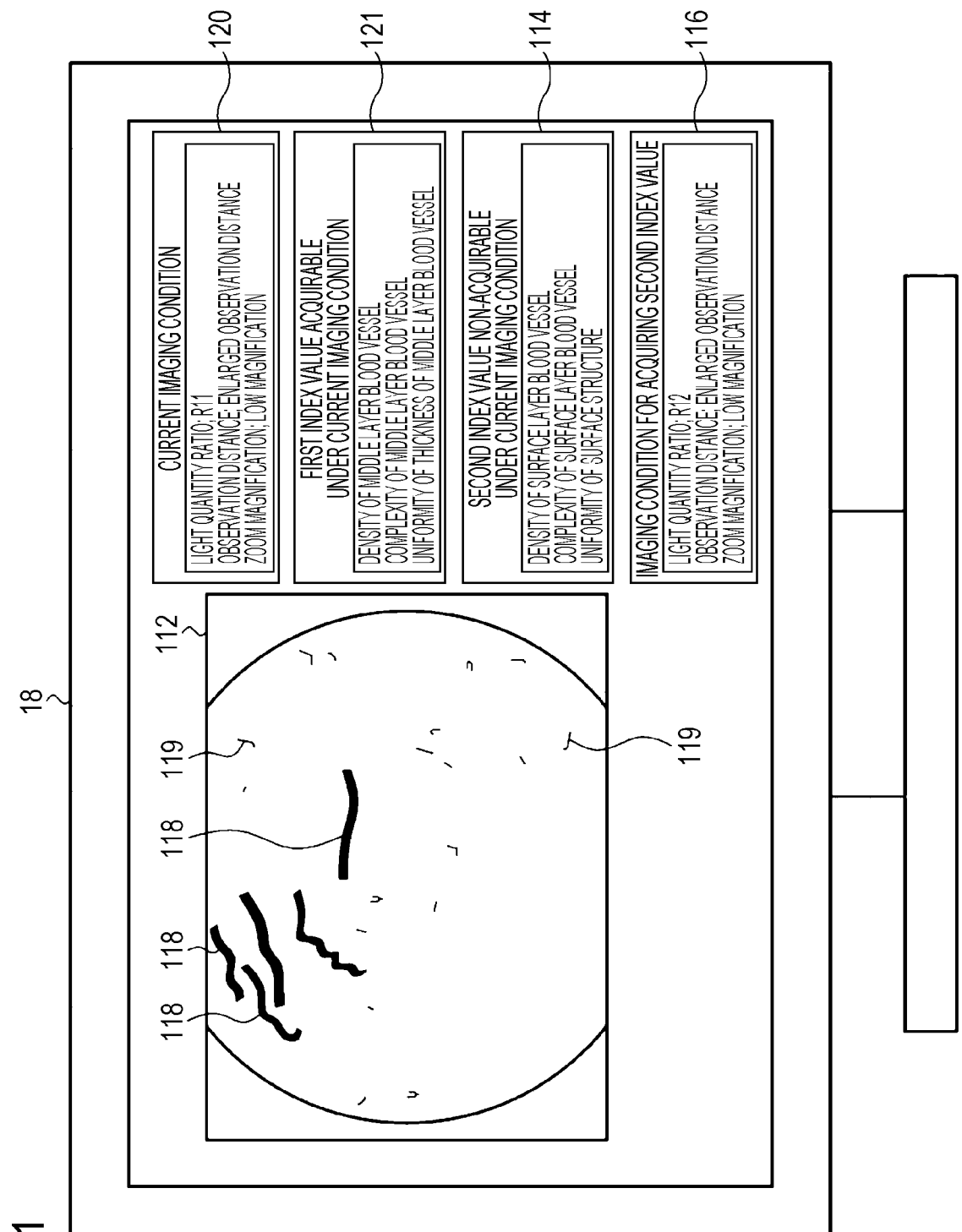
FIG. 11 illustrates another display screen of the display unit.

As illustrated in FIG. 11, the display control unit 62 controls the display unit 18 to further display, for example, information 120 indicating the current first imaging condition and information 121 indicating the first index value acquirable under the current first imaging condition, in addition to the information 114 indicating the second index value non-acquirable under the current first imaging condition and the information 116 indicating the second imaging condition for acquiring the second index value. By displaying the first imaging condition and the second index value on the display unit 18 in this way, guidance indicating that the second index value is non-acquirable under the current first imaging condition is displayed. Further, by displaying the first imaging condition and the second imaging condition on the display unit 18, guidance display of specific setting for changing the current first imaging condition into the second imaging condition is provided.

Second Embodiment

In the above-described first embodiment, the imaging condition extraction unit 76 extracts the second imaging condition under which the index value non-acquirable under the first imaging condition is acquirable; however, in a second embodiment, the imaging condition extraction unit 76 extracts an imaging condition under which the second index value that is non-acquirable under the first condition and that is suitable for the diagnosis purpose is acquirable.

Figure 12:
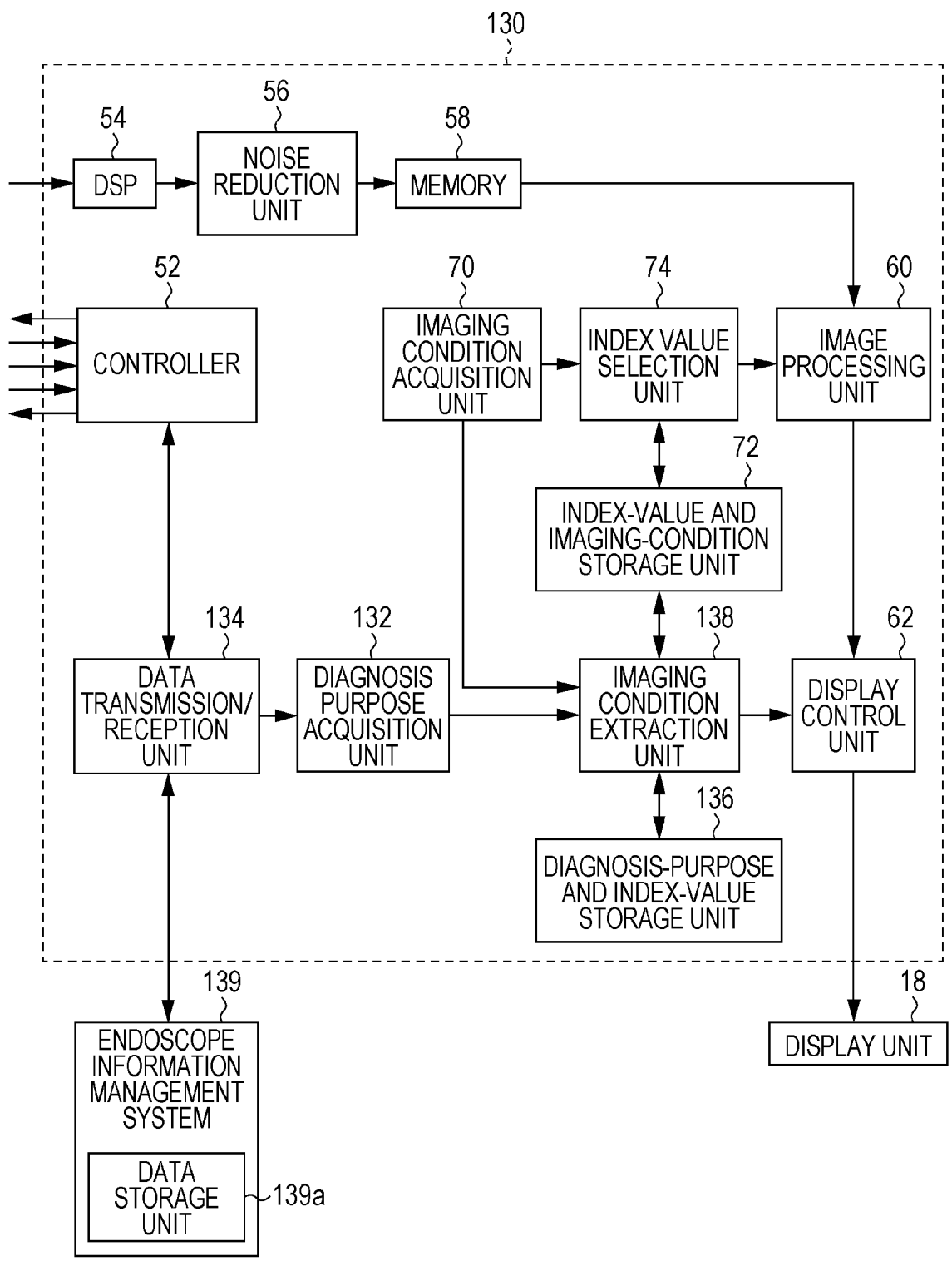
FIG. 12 is a block diagram explaining a processor device according to a second embodiment.

As illustrated in FIG. 12, in the second embodiment, a processor device 130 is used instead of the processor device 16 of the above-described first embodiment. The processor device 130 has, in addition to the respective units of the processor device 16, a diagnosis purpose acquisition unit 132, a data transmission/reception unit 134, and a diagnosis-purpose and index-value storage unit 136. In addition, the processor device 130 is provided with an imaging condition extraction unit 138 instead of the imaging condition extraction unit 76.

The diagnosis purpose acquisition unit 132 acquires a diagnosis purpose from an endoscope information management system 139 connected to the diagnosis purpose acquisition unit 132 so as to communicate with each other through a network such as a local area network (LAN) via the data transmission/reception unit 134. The endoscope information management system 139 is a file server of a system such as a picture archiving and communication system (PACS) that files endoscope images. The endoscope information management system 139 has a data storage unit 139a that stores, as endoscope information management data, inspection information including a diagnosis purpose input from an input terminal (not illustrated), patient information, and so forth. The diagnosis purpose acquisition unit 132 receives the endoscope information management data from the data storage unit 139a, and acquires the diagnosis purpose by extracting the diagnosis purpose from the endoscope information management data. The diagnosis purpose acquisition unit 132 inputs the acquired diagnosis purpose to the imaging condition extraction unit 76.

The diagnosis-purpose and index-value storage unit 136 stores a plurality of index values on a diagnosis purpose basis. Diagnosis purposes include a first diagnosis purpose including screening and close inspection, a second diagnosis purpose relating to the type of disease, and a third diagnosis purpose relating to the stage of disease. The first diagnosis purpose is not limited to the above-described screening and close inspection, and there are a variety of diagnosis purposes. For example, the first diagnosis purpose includes treatment, post-treatment surveillance, and so forth.

As illustrated in FIG. 13, the diagnosis-purpose and index-value storage unit 136 has first to third index value selection tables 136a to 136c. The first index value selection table 136a stores a first diagnosis purpose and an index value that is used for the first diagnosis purpose in an associated manner. For example, in the first index value selection table 136a, large intestine screening is associated with the complexity of a surface layer blood vessel and the complexity of a middle layer blood vessel; stomach screening is associated with the complexity of a middle layer blood vessel and the uniformity of a surface structure; and large intestine close inspection is associated with the density of a surface layer blood vessel.

The second index value selection table 136b stores a second diagnosis purpose and an index value that is used for the second diagnosis purpose in an associated manner. For example, in the second index value selection table 136b, Barrett's esophagus is associated with the density of a surface layer blood vessel, the complexity of a surface layer blood vessel, the density of a middle layer blood vessel, and the complexity of a middle layer blood vessel; large intestinal polyposis is associated with the uniformity of the thickness of a middle layer blood vessel and the uniformity of a surface structure; and angiodysplasia is associated with the density of a middle layer blood vessel.

The third index value selection table 136c stores a third diagnosis purpose and an index value that is used for the third diagnosis purpose in an associated manner. For example, in the third index value selection table 136c, the remission period of ulcerative colitis is associated with the complexity of a surface layer blood vessel and the complexity of a middle layer blood vessel; and the active period of ulcerative colitis is associated with the complexity of a surface layer blood vessel.

The correspondences stored in the first to third index value selection tables 136a to 136c can be appropriately updated, for example, through an input operation with the instruction input part 19. Moreover, new correspondences can be added to the first to third index value selection tables 136a to 136c.

The imaging condition extraction unit 138 uses the second index value that is non-acquirable under the first imaging condition and that is used for the acquired diagnosis purpose, and extracts the second imaging condition. To be specific, the imaging condition extraction unit 138 extracts the second imaging condition in accordance with at least one diagnosis purpose of the first diagnosis purpose, the second diagnosis purpose, or the third diagnosis purpose. To be more specific, the imaging condition extraction unit 138 refers to the first index value selection table 136*a* of the diagnosis-purpose and index-value storage unit 136 when acquiring the first diagnosis purpose; refers to the second index value selection table 136*b* when acquiring the second diagnosis purpose; and refers to the third index value selection table 136*c* when acquiring the third diagnosis purpose.

The imaging condition extraction unit 138 first refers to the diagnosis-purpose and index-value storage unit 136, and selects the index value that is used for the diagnosis purpose acquired by the diagnosis purpose acquisition unit 132. For example, when the acquired second diagnosis purpose is large intestinal polyposis, the imaging condition extraction unit 138 selects the uniformity of the thickness of a middle layer blood vessel and the uniformity of a surface structure from the second index value selection table 136*b*.

Figure 14:
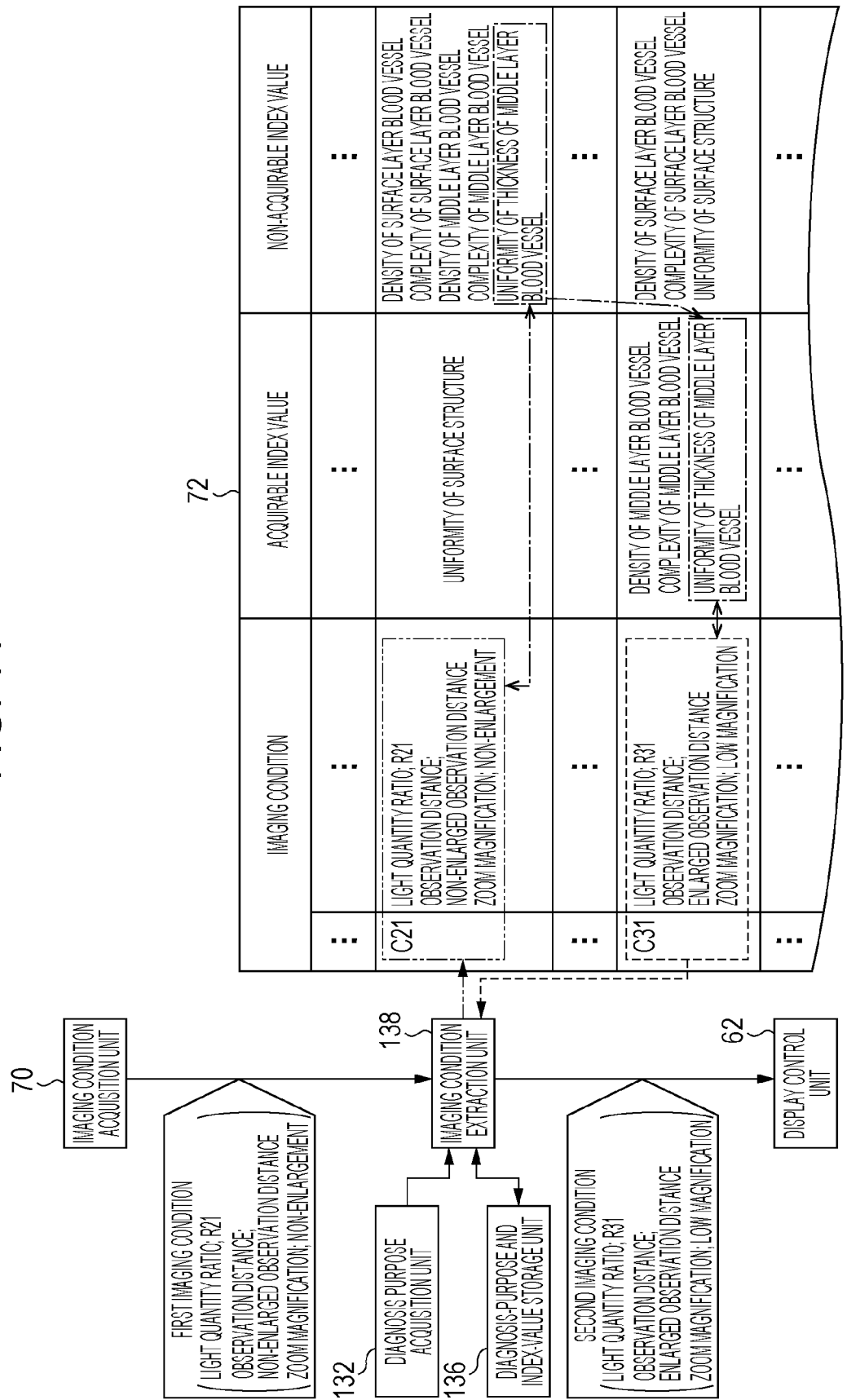
FIG. 14 is an illustration explaining an imaging condition extraction unit according to the second embodiment.

As illustrated in FIG. 14, the imaging condition extraction unit 138 extracts an imaging condition C21 that meets the first imaging condition similarly to the first embodiment. In FIG. 14, a light quantity ratio R21 is 1:0:0:0. Thus, with the light quantity ratio R21, violet light LV is emitted as illumination light. When index values non-acquirable under the extracted imaging condition C21 include an index value that is used for the diagnosis purpose, the imaging condition extraction unit 138 selects the index value that is used for the diagnosis purpose as a second index value. When the index values non-acquirable under the extracted imaging condition C21 do not include the index value that is used for the diagnosis purpose, the imaging condition extraction unit 138 performs processing similar to the first embodiment. In this embodiment, the uniformity of the thickness of a middle layer blood vessel to be used for the diagnosis of large intestine polyposis is the index value non-acquirable under the imaging condition C21, and the uniformity of a surface structure is acquirable under the imaging condition C21. Thus, the imaging condition extraction unit 138 selects the uniformity of the thickness of a middle layer blood vessel as the second index value. The imaging condition extraction unit 138 extracts, as the second imaging condition, an imaging condition C31 under which the selected uniformity of the thickness of a middle layer blood vessel is acquirable from among the plurality of imaging conditions. In FIG. 14, a light quantity ratio R31 is 0:1:0:0. Thus, with the light quantity ratio R31, blue light LB is emitted as illumination light. The imaging condition extraction unit 138 inputs the extracted second imaging condition to the display control unit 62. The display control of the display control unit 62 is similar to that of the above-described first embodiment. By providing the guidance display indicating that the index value that is used for the diagnosis purpose is non-acquirable under the current imaging condition in this way, the index value suitable for the diagnosis purpose is further reliably acquired.

Figure 15:
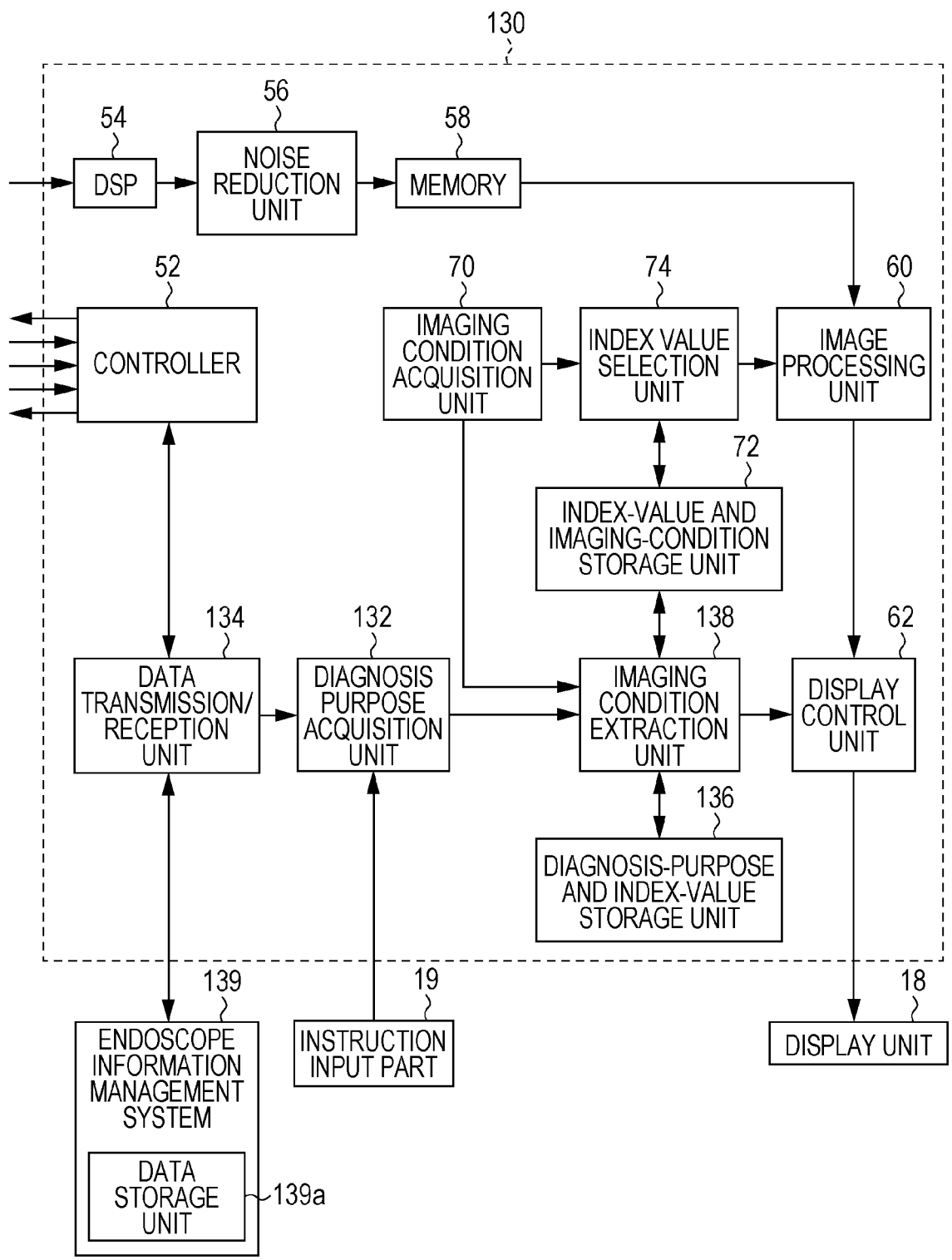
FIG. 15 is an illustration explaining acquisition of a diagnosis purpose from an instruction input part.

While the diagnosis purpose acquisition unit 132 acquires the diagnosis purpose from the endoscope information management system 139 through the network in the above-described second embodiment, as illustrated in FIG. 15, the diagnosis purpose acquisition unit 132 may acquire a diagnosis purpose input from the instruction input part 19 serving as a diagnosis purpose input unit, in addition to acquiring the diagnosis purpose from the endoscope information management system 139. In this case, the imaging condition extraction unit 138 uses the diagnosis purpose input from the instruction input part 19 with higher priority. Thus, during a diagnosis, the diagnosis purpose can be switched to a diagnosis purpose that is different from the diagnosis purpose acquired from the endoscope information management system 139, and the inspection can be continued.

Alternatively, the diagnosis purpose acquisition unit 132 may acquire the diagnosis purpose input from the instruction input part 19 instead of acquiring the diagnosis purpose from the endoscope information management system 139. In this case, the diagnosis purpose can be acquired even when the diagnosis purpose acquisition unit 132 is not connected to the endoscope information management system 139 through the network.

Third Embodiment

Figure 16:
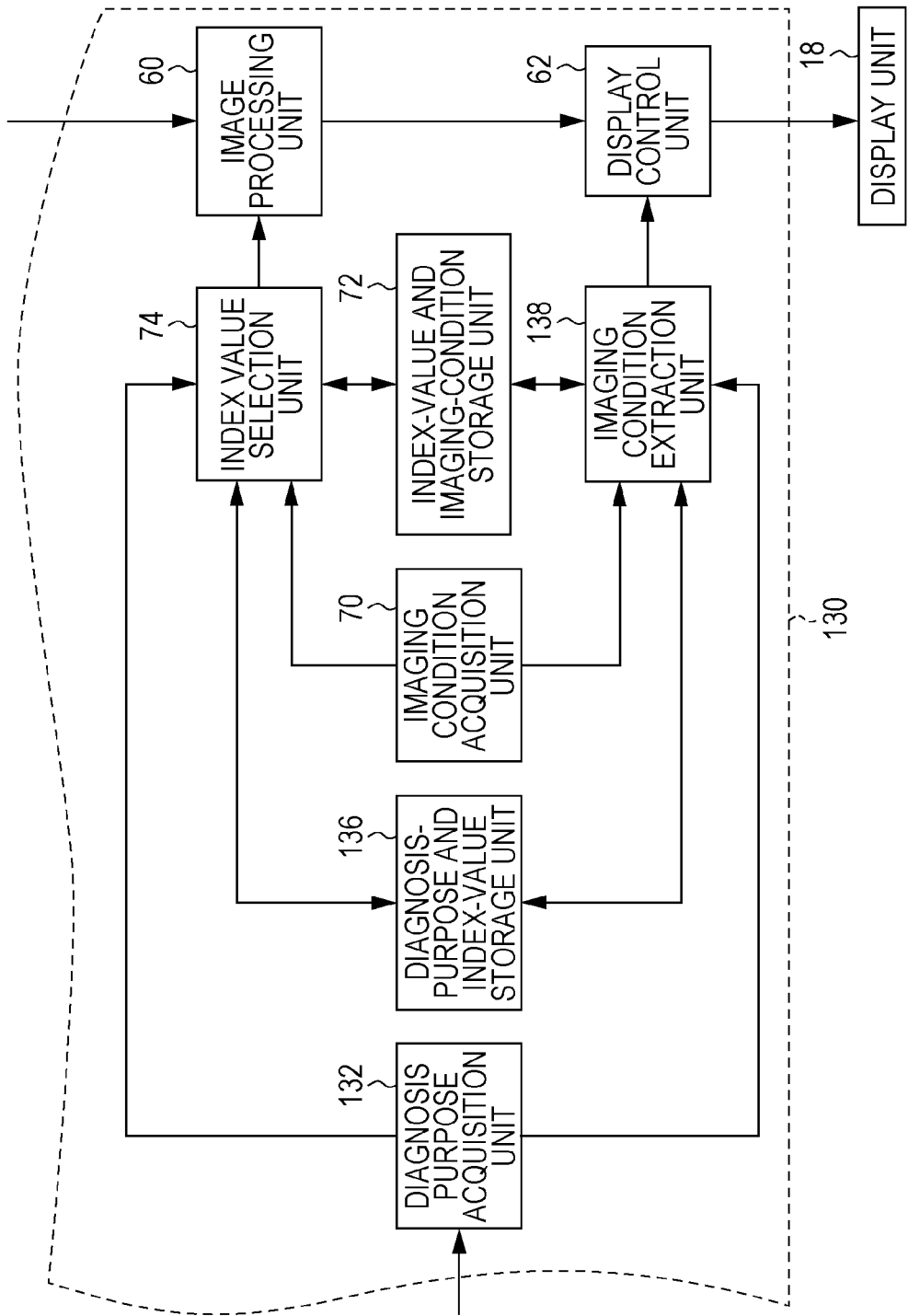
FIG. 16 is a block diagram explaining a processor device according to a third embodiment.

In the above-described second embodiment, the diagnosis purpose is used when the second imaging condition is extracted. In contrast, in a third embodiment, the diagnosis purpose is used when the first index value is selected. As illustrated in FIG. 16, in the third embodiment, the diagnosis purpose acquisition unit 132 inputs the acquired diagnosis purpose to the index value selection unit 74.

The index value selection unit 74 refers to the diagnosis-purpose and index-value storage unit 136 and selects, as the first index value, an index value that is acquirable under the first imaging condition and that is used for the acquired diagnosis purpose. The index value selection unit 74 inputs the selected first index value to the index value calculation unit 108. The subsequent processing is similar to that of the first embodiment, and hence the description is omitted. In the third embodiment, the structure emphasis image generated by the emphasis image generation unit 110 is displayed in an emphasized manner by using the first index value that is used for the diagnosis purpose. Moreover, the display control unit 62 may provide guidance display indicating that the first index value that is used for the diagnosis purpose is acquirable under the current first imaging condition.

Fourth Embodiment

In the above-described third embodiment, the emphasis display is provided by using the first index value that is used for the diagnosis purpose. In contrast, in a fourth embodiment, a structure parameter is calculated by using an index value, and emphasis display using the structure parameter is provided.

As illustrated in FIG. 17, in the fourth embodiment, a diagnosis-purpose and index-value storage unit 142 is provided instead of the diagnosis-purpose and index-value storage unit 136. The diagnosis-purpose and index-value storage unit 142 stores, in addition to the diagnosis purpose and the index value, a weighting coefficient that is used by a structure parameter calculation unit 146 (described later) in an associated manner. The diagnosis-purpose and index-value storage unit 142 has first to third index value selection tables 142*a* to 142*c*. Regarding the first to third index value selection tables 142*a* to 142*c*, the relationship between the diagnosis purpose and the index value is the same as that of the diagnosis-purpose and index-value storage unit 136, and hence the description thereof is omitted. The relationship with the weighting coefficient (hereinafter, referred to as coefficient) is described below.

The first index value selection table 142*a* stores a first diagnosis purpose, an index value that is used for the first diagnosis purpose, and a coefficient per index value in an associated manner. For example, regarding large intestine screening, the coefficient for the complexity of a surface layer blood vessel is 0.5, and the coefficient for the complexity of a middle layer blood vessel is 1. Regarding stomach screening, the coefficient for the complexity of a middle layer blood vessel is 1, and the coefficient for the uniformity of a surface structure is 1. Regarding large intestine close inspection, the coefficient for the density of a surface layer blood vessel is 1.

The second index value selection table 142b stores a second diagnosis purpose, an index value that is used for the second diagnosis purpose, and a coefficient per index value in an associated manner. For example, regarding Barrett's esophagus, the coefficient for the density of a surface layer blood vessel, the coefficient for the complexity of a surface layer blood vessel, the coefficient for the density of a middle layer blood vessel, and the coefficient for the complexity of a middle layer blood vessel each are 1. Regarding large intestinal polyposis, the coefficient for the uniformity of the thickness of a middle layer blood vessel is 1, and the coefficient for the uniformity of a surface structure is 0.5. Regarding angiodysplasia, the coefficient for the density of a middle layer blood vessel is 1.

The third index value selection table 142c stores a third diagnosis purpose, an index value that is used for the third diagnosis purpose, and a coefficient per index value in an associated manner. For example, regarding the remission period of ulcerative colitis, the coefficient for the complexity of a surface layer blood vessel and the coefficient for the complexity of a middle layer blood vessel each are 1. Regarding the active period of ulcerative colitis, the coefficient for the complexity of a surface layer blood vessel is 1.

The correspondences stored in the first to third index value selection tables 142a to 142c can be appropriately updated, for example, through an input operation with the instruction input part 19. Moreover, new correspondences can be added to the first to third index value selection tables 142a to 142c.

In this embodiment, the diagnosis purpose acquisition unit 132 acquires one of the first to third diagnosis purposes. However, the diagnosis purpose acquisition unit 132 may acquire a composite purpose in which a plurality of diagnosis purposes such as the first diagnosis purpose and the second diagnosis purpose are combined. To prepare for such a case, the diagnosis-purpose and index-value storage unit 142 may be provided with a table for a composite purpose. The table for a composite purpose stores a composite purpose, index values that are used for the composite purpose, and a coefficient per index value in an associated manner. The index values that are used for the composite purpose are index values that are used for respective diagnosis purposes constituting the composite purpose. The coefficient stored in the table for a composite purpose is set, for example, to a larger value for index values that overlap one another by a larger number among the index values that are used for the respective diagnosis purposes constituting the composite purpose.

The index value selection unit 74 refers to the diagnosis-purpose and index-value storage unit 142 and selects, as the first index value, an index value that is acquirable under the first imaging condition and that is used for the acquired diagnosis purpose. The index value selection unit 74 inputs the selected first index value to the index value calculation unit 108. The index value calculation unit 108 calculates the first index value selected by the index value selection unit 74 similarly to the above-described first embodiment.

Figure 18:
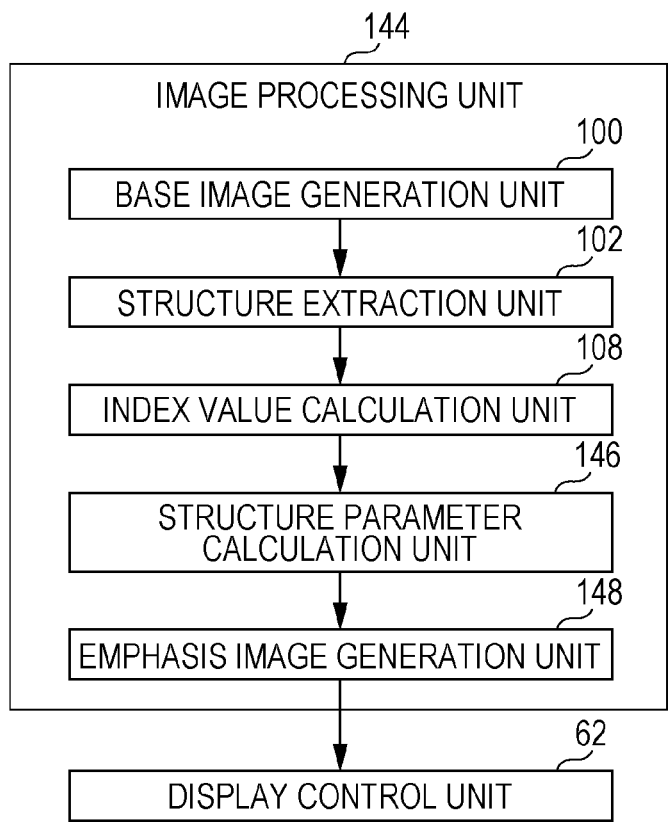
FIG. 18 is a block diagram explaining an image processing unit according to the fourth embodiment.

In the fourth embodiment, an image processing unit 144 illustrated in FIG. 18 is included instead of the image processing unit 60 of the third embodiment. The image processing unit 144 has, in addition to the respective units of the image processing unit 60 of the third embodiment, a structure parameter calculation unit 146, and has an emphasis image generation unit 148 instead of the emphasis image generation unit 110.

The structure parameter calculation unit 146 calculates a structure parameter by using the first index value calculated by the index value calculation unit 108. To be specific, the structure parameter calculation unit 146 calculates a structure parameter by weighting a plurality of first index values with a coefficient (weighting coefficient) determined in accordance with the diagnosis purpose and arithmetically operating the first index values. The structure parameter calculation unit 146, when calculating the structure parameter, refers to the diagnosis-purpose and index-value storage unit 142 and uses the coefficient associated with the first index value calculated by the index value calculation unit 108.

The structure parameter is a numerical value that is calculated by using index values in such a way of imitating the viewpoint of a doctor who carries out a diagnosis with regard to the entirety of the index values. For example, the structure parameter is calculated through arithmetic operation such as addition of index values having mutually different dimensions (units), and hence the structure parameter has no physical meaning; however, the structure parameter functions as an index of a diagnosis. That is, the structure parameter differs from the index value in that the structure parameter has no physical meaning.

For example, when the second diagnosis purpose acquired by the diagnosis purpose acquisition unit 132 is Barrett's esophagus, the structure parameter calculation unit 146 calculates a structure parameter by multiplying each of the density of a surface layer blood vessel, the complexity of a surface layer blood vessel, the density of a middle layer blood vessel, and the complexity of a middle layer blood vessel by 1 and adding these values. While the structure parameter calculation unit 146 calculates a single structure parameter by using a plurality of index values in this embodiment, it is not limited thereto, and the structure parameter calculation unit 146 may calculate two or more structure parameters. The structure parameter may be calculated by any method. For example, without being limited to the calculation of the structure parameter using the weighted sum of the plurality of index values as described above, a structure parameter may be calculated through arithmetic operation involving mixture of at least two of addition, subtraction, multiplication, and division, or a structure parameter may be calculated by using any of other functions. Further, the structure parameter calculation unit 146 may calculate a structure parameter by multiplying a single index value by a weighting coefficient.

The emphasis image generation unit 148 uses the generated base image and the calculated structure parameter, and generates a structure emphasis image serving as a second structure emphasis image. The emphasis image generation unit 148 generates a structure emphasis image, for example, by performing overlap processing of overlaying information based on the structure parameter, on the base image. The emphasis image generation unit 148 corresponds to a second emphasis image generation unit of the present invention.

Figure 19:
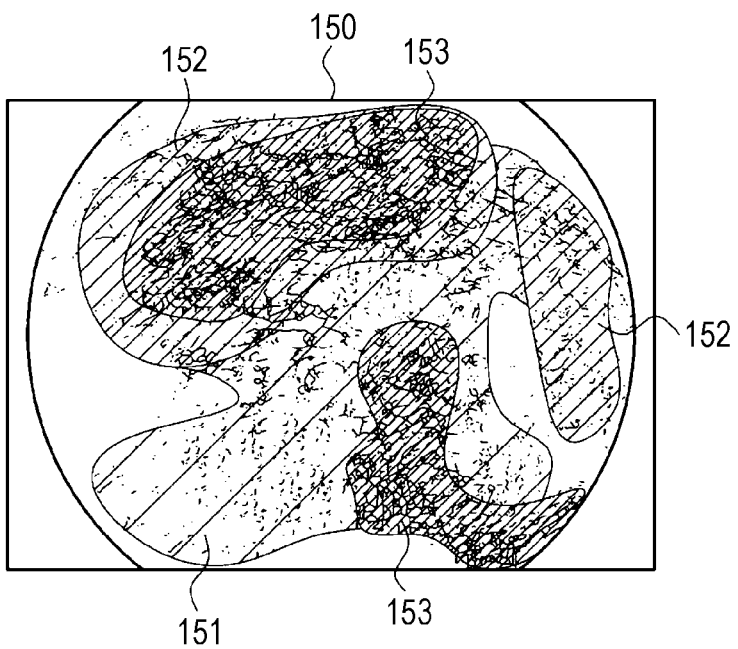
FIG. 19 illustrates a structure emphasis image displayed in an emphasized manner by using a structure parameter.

For example, in a structure emphasis image 150 illustrated in FIG. 19, regions 151 to 153 are displayed with different colors in accordance with the structure parameters.

For example, the region 151 among the regions 151 to 153 has the smallest structure parameter and hence has a blue-based color. The region 152 has a larger structure parameter than the region 151 and hence has a yellow-based color. The region 153 has a larger structure parameter than the region 152 and hence has a red-based color. In this case, information indicating the value of the structure parameter may be overlaid on the base image. Thus, a structure suitable for the diagnosis purpose can be further emphasized.

Some index values among a plurality of index values that are used for calculating a structure parameter may not be occasionally acquired under the current imaging condition. In such a case, for example, by multiplying a first index value acquirable under the current imaging condition by a specific coefficient, the structure parameter may be calculated with use of only the first index value. The specific coefficient is, for example, predetermined by machine learning and stored in the diagnosis-purpose and index-value storage unit 142.

In each of the above-described embodiments, when the guidance of the second imaging condition is displayed on the display unit 18, the guidance is displayed as text information. Additionally or alternatively, an icon recognizably indicating that the second index value is acquirable under the second imaging condition may be displayed. For example, when the light quantity ratio is displayed as the second imaging condition, the color of the light source may be displayed with a color bar or the like. When the zoom magnification is displayed as the second imaging condition, a magnifying glass or the like may be displayed. When the observation distance is displayed as the second imaging condition, animation or the like that moves an endoscope toward or away from an observation object may be displayed. In addition to or instead of the guidance display on the display unit 18, the state in which the second index value is acquirable under the second imaging condition may be informed with voice guide through a loudspeaker.

REFERENCE SIGNS LIST 10 endoscope system
12 endoscope
12a insertion section
12b operation section
14 light source device
16 processor device
18 display unit
21 instruction input part
21 distal end portion
22 bending portion
23 flexible pipe portion
25 angle knob
26 image storage operating unit
27 mode switching unit
28 zoom operating unit
30 light source
30a V-LED
30b B-LED
30c G-LED
30d R-LED
30e optical filter
32 light source control unit
34 light guide
36 illumination optical system
38 image pick-up optical system
40 illumination lens
42 objective lens
44 zoom lens
46 image pick-up sensor
48 CDS/AGC circuit
50 A/D conversion circuit
52 controller
54 DSP
56 noise reduction unit
58 memory
60 image processing unit
62 display control unit
70 imaging condition acquisition unit
72 index-value and imaging-condition storage unit
74 index value selection unit
76 imaging condition extraction unit
100 base image generation unit
102 structure extraction unit
104 index value storage unit
108 index value calculation unit
110 emphasis image generation unit
112 structure emphasis image
114 information
116 information
118 region
119 surface layer blood vessel
120 information
121 information
130 processor device
132 diagnosis purpose acquisition unit
134 data transmission/reception unit
136 diagnosis-purpose and index-value storage unit
136a first index value selection table
136b second index value selection table
136c third index value selection table
138 imaging condition extraction unit
139 endoscope information management system
139a data storage unit
142 diagnosis-purpose and index-value storage unit
142a first index value selection table
142b second index value selection table
142c third index value selection table
144 image processing unit
146 structure parameter calculation unit
148 emphasis image generation unit
150 structure emphasis image
151 region
152 region
153 region

What is claimed is:

1. An endoscope system comprising:
a storage medium that stores a plurality of correspondence between an imaging condition and a plurality of index values relating to a plurality of structures of an observation object, wherein the plurality of index values including a first index value acquirable under the first imaging condition and a second index value non-acquirable under the first imaging condition but acquirable under a second imaging condition;
a monitor; and
a processor, coupled to the storage medium and the monitor, wherein e processor is configured to:
acquire an image of the observation object by using an endoscope;
acquire a first imaging condition which represents an imaging condition of the image;

refer to the plurality of index values and the imaging condition in the storage medium, and extract the second imaging condition according to the first imaging condition, and display guidance indicating that the second index value is acquirable under the extracted second imaging condition.

2. The endoscope system according to claim 1, wherein the processor is further configured to:
acquire a diagnosis purpose, wherein the diagnosis purpose comprising a composite purpose that corresponds to a coefficient stored in a table for the composite purpose, wherein the table stores the index values in association with the composite purpose, and the coefficient which associates the index values with the composite purpose, and
use the second index value that is non-acquirable under the first imaging condition and that is used for the acquired diagnosis purpose, and extract the second imaging condition.

3. The endoscope system according to claim 2,
wherein the diagnosis purpose includes a first diagnosis purpose including screening and close inspection, a second diagnosis purpose relating to a type of disease, and a third diagnosis purpose relating to a stage of disease, and
wherein the processor is further configured to extract the second imaging condition in accordance with at least one diagnosis purpose of the first diagnosis purpose, the second diagnosis purpose, or the third diagnosis purpose.

4. The endoscope system according to claim 3, wherein the processor is further configured to display the acquired first imaging condition.

5. The endoscope system according to claim 2, wherein the processor is further configured to display the acquired first imaging condition.

6. The endoscope system according to claim 1, wherein the processor is further configured to:
use the acquired first imaging condition, refers to the index-value and imaging-condition storage unit, and selects the first index value; and
display guidance indicating that the first index value is acquirable under the acquired first imaging condition.

7. The endoscope system according to claim 6, wherein the processor is further configured to:
acquire a diagnosis purpose, and
select, as the first index value, an index value that is acquirable under the first imaging condition and that is used for the acquired diagnosis purpose.

8. The endoscope system according to claim 7, wherein the processor is further configured to:
acquire an endoscope image obtained through the imaging;
calculate the selected first index value from the endoscope image; and
use the endoscope image and the calculated index value, and generates a first structure emphasis image in which the structure is emphasized.

9. The endoscope system according to claim 8, wherein the processor is further configured to calculate a structure parameter of the structure by weighting the calculated first index value and arithmetically operating the first index value.

10. The endoscope system according to claim 9, wherein the processor is further configured to use the endoscope image and the calculated structure parameter, and generates a second structure emphasis image in which the structure is emphasized.

11. The endoscope system according to claim 8, wherein the processor is further configured to display the acquired first imaging condition.

12. The endoscope system according to claim 7, wherein the processor is further configured to display the acquired first imaging condition.

13. The endoscope system according to claim 6, wherein the processor is further configured to:
acquire an endoscope image obtained through the imaging;
calculate the selected first index value from the endoscope image; and
use the endoscope image and the calculated index value, and generates a first structure emphasis image in which the structure is emphasized.

14. The endoscope system according to claim 13, wherein the processor is further configured to calculate a structure parameter of the structure by weighting the calculated first index value and arithmetically operating the first index value.

15. The endoscope system according to claim 14, wherein the processor is further configured to use the endoscope image and the calculated structure parameter, and generates a second structure emphasis image in which the structure is emphasized.

16. The endoscope system according to claim 13, wherein the processor is further configured to display the acquired first imaging condition.

17. The endoscope system according to claim 6, wherein the processor is further configured to display the acquired first imaging condition.

18. The endoscope system according to claim 1, wherein the processor is further configured to display the acquired first imaging condition.

19. The endoscope system according to claim 1, wherein the plurality of index values comprising at least one of a density of the structure, uniformity of the structure and complexity of the structure.

20. The endoscope system according to claim 1, wherein the imaging condition comprising at least one of a light quantity ratio of light sources, an observation distance with respect to the observation object and a zoom magnification of the endoscope.

21. An operating method of an endoscope system, the method comprising:
a step of storing a plurality of correspondence between an imaging condition and a plurality of index values relating to a plurality of structures of an observation object, wherein the plurality of index values including a first index value acquirable under the first imaging condition and a second index value non-acquirable under the first imaging condition but acquirable under a second imaging condition;
a step of acquiring an image of the observation object by using an endoscope;
a step of acquiring a first imaging condition which represents an imaging condition of the image;
a step of referring to the plurality of index values and the imaging condition in the storage medium;
a step of extracting the second imaging condition; and
a step of displaying guidance indicating that the second index value is acquirable under the extracted second imaging condition.

22. An endoscope system comprising:
a storage medium that stores a plurality of correspondence between an imaging condition and a plurality of index values relating to a plurality of structures of an observation object, wherein the plurality of index values including a first index value acquirable under the first imaging condition and a second index value non-acquirable under the first imaging condition but acquirable under a second imaging condition;
a monitor; and
a processor, coupled to the storage medium and the monitor, wherein the processor is configured to:
  acquire an image of the observation object by using an endoscope;
  acquire a first imaging condition which represents an imaging condition of the image;
  use the acquired first imaging condition, and refer to the plurality of index values and the imaging condition in the storage medium, and select the first index value;
calculate the selected first index value from the image;
use the image and the calculated index value, and generates a first structure emphasis image in which the structure is emphasized;
refer to the plurality of index values and the imaging condition in the storage medium, and extract the second imaging condition; and
display the first structure emphasis image and displays guidance indicating that the second index value is acquirable under the extracted second imaging condition.

* * * * *